United States Patent
Weeber et al.

(10) Patent No.: US 9,962,426 B2
(45) Date of Patent: *May 8, 2018

(54) REELIN RESCUES COGNITIVE FUNCTION

(71) Applicants: Edwin Weeber, Apollo Beach, FL (US); Lisa Zhao, Alhambra, CA (US); Melinda Peters, Riverview, FL (US)

(72) Inventors: Edwin Weeber, Apollo Beach, FL (US); Lisa Zhao, Alhambra, CA (US); Melinda Peters, Riverview, FL (US)

(73) Assignees: University of South Florida, Tampa, FL (US); Vanderbilt University, Nashville, TN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/969,959

(22) Filed: Dec. 15, 2015

(65) Prior Publication Data

US 2016/0271213 A1 Sep. 22, 2016

Related U.S. Application Data

(63) Continuation of application No. 13/206,174, filed on Aug. 9, 2011, now Pat. No. 9,241,975, which is a continuation of application No. PCT/US2010/023615, filed on Feb. 9, 2010.

(60) Provisional application No. 61/150,890, filed on Feb. 9, 2009.

(51) Int. Cl.
| | |
|---|---|
| A61K 39/395 | (2006.01) |
| A61K 39/40 | (2006.01) |
| A61K 39/42 | (2006.01) |
| A61K 38/17 | (2006.01) |
| A61K 38/53 | (2006.01) |

(52) U.S. Cl.
CPC .......... *A61K 38/1709* (2013.01); *A61K 38/53* (2013.01)

(58) Field of Classification Search
None
See application file for complete search history.

(56) References Cited

U.S. PATENT DOCUMENTS 9,241,975 B2 * 1/2016 Weeber ............ A61K 38/1709

OTHER PUBLICATIONS

Bucic, Marina, et al. Completed suicide, depression, and RELN polymorphisms. Psychiatric Genetics, Oct. 2016, vol. 26, No. 5, pp. 218-222.

Bufill, Enric, et al. Reelin Signaling Pathway Genotypes and Alzheimer Disease in a Spanish Population. Alzheimer Disease & Associated Disorders, Apr.-Jun. 2015, vol. 29, Issue 2, pp. 169-172.
Chen, Na, et al. Meta-analyses of RELN variants in neuropsychiatric disorders. Behavioural Brain Research (2017) 110-119.
Fatemi, SH, et al. Reduction in Reelin immunoreactivity in hippocampus of subjects with schizophrenia, bipolar disorder and major depression. Molecular Psychiatry (2000) 5, 654-663.
Goes, F.S., et al. Sex-Specific Association of the Reelin Gene With Bipolar Disorder. Am J Med Genet B Neurophsyciatr Genet Mar. 5, 2010; 153B(2): 549-553.
Guidotti, Alessandro, et al. Decrease in Reelin and Glutamic Acid Decarboxylase67 (GAD67) Expression in Schizophrenia and Bipolar Disorder. Arch Gen Psychiatry, Nov. 2000, vol. 57, pp. 1061-1070.
Hethorn, Whitney R., et al. Reelin supplementation recovers synaptic plasticity and cognitive deficits in a mouse model for Angelman syndrome. European Journal of Neuroscience, 2015, vol. 41, pp. 1372-1380.
Hornig, Tobias, et al. Increased Blood-Reelin-Levels in First Episode Schizophrenia. PLoS One, Aug. 25, 2015; 10(8). DOI:10.1371/journal.pone.0134671.
Hu, Chunli, et al. Neuroprotective effect of melatonin on soluble ABeta1-42-induced cortical neurodegeneration via Reelin-Dab1 signaling pathway. Neurological Research, Jul. 2017, vol. 39, No. 7, 621-631.
Impagnatiello, Frencesco, et al. A decrease of reelin expression as a putative vulnerability factor in schizophrenia. Proc. Natl. Acad. Sci. Dec. 1998, vol. 95, pp. 15718-15723.
Jordan, ChaRandle, et al. Cerebellar gene expression profiles of mouse models for Rett syndrome reveal novel MeCP2 targets. BMC Medical Genetics 2007, 8:36.
Lane-Donovan, Courtney, et al. Reelin protects against amyloid Beta toxicity in vivo. Sci Signal, Jul. 7, 2015; 8(384):ra67.
Li, Ming, et al. Convergent Lines of Evidence Support LRP8 as a Susceptibility Gene for Psychosis. Mol Neurobiol, Dec. 2016; 53(10):6608-6619.

(Continued)

*Primary Examiner* — Olga N Chernyshev
(74) *Attorney, Agent, or Firm* — Michael L. Lawson; Smith & Hopen, P.A.

(57) ABSTRACT

Disclosed are methods of influencing, and enhancing, cognitive function by increasing, and/or preventing interference with, Reelin levels as well as Reelin signaling. Cognitive function is improved, in a subject in need thereof, by administering a therapeutically effective amount of Reelin, a Reelin-specific modulator or an agonist of a lipoprotein receptor to the subject. The lipoprotein receptor can be selected from candidates such as ApoER2 and VLDLR. As disclosed herein, agonists of the lipoprotein receptor for use with the inventive method include APC, Sep and Fc-RAP. In addition to administering exogenous Reelin, a Reelin-specific modulator, such as a recombinant Reelin fragment, can be used to increase Reelin levels and/or signaling.

5 Claims, 41 Drawing Sheets

(56) References Cited

OTHER PUBLICATIONS

Lorenzetto, Erika, et al. Impaird nerve regeneration in reeler mice after peripheral nerve injury. European Journal of Neuroscience, 2008, vol. 27, pp. 12-19.

Lussier, April L., et al. Reelin Proteolysis Affects Signaling Related to Normal Synapse Function and Neurodegeneration. Frontiers in Cellular Neuroscience, Mar. 2016, vol. 10, Article 72.

Mata, Agata, et al. Reelin Expression in Creutzfeldt-Jakob Disease and Experimental Models of Transmissible Spongiform Encephalopathies. Mol Neurobiol, 2017; 54:6412-6425.

Miyashita, A., et al. Genes associated with the progression of neurofibrillary tangles in Alzheimers disease. Transl Psychiatry (2014) 4, 1-8.

Stary, Creed M., et al. miR-200c Contributes to Injury From Transient Focal Cerebral Ischemia by Targeting Reelin. Stroke, Febuary 2015; 46(2); 551-556.

Valence, S., et al. RELN and VLDLR mutations underlie two distinguishable clinico-radiological phenotypes. Clin Genet 2016: 90: 545-549.

Veldic, Marin, et al. Epigenetic mechanisms expressed in basal ganglia GABAergic neurons differentiate schizophrenia from bipolar disorder. Schizophr Res. Mar. 2007; 91(1-3): 51-61.

Won, Seok Joon, et al. Reelin-deficient mice show impaired neurogenesis and increased stroke size. Experimental Neurology 198 (2006) 250-259.

Zhou, Zhifan, et al. Identification of RELM variation p. Thr3192Ser in a Chinese family with schizophrenia. Scientific Reports, Apr. 13, 2016; 6:24327.

Knuesel, Irene. Reelin-mediated signaling in neuropsychiatric and neurodegenerative diseases. Progress in Neurobiology. 2010. vol. 91: 257-274.

\* cited by examiner

Cellular

Supernatant

| Antibody | Recognition Site | Animal Source | Commercial Source |
|---|---|---|---|
| G10 | 164-496 | Ms, mAb | Chemicon, MAB5364 |
| G20 | C-terminus | Gt, pAb | SCBT, sc-7741 |
| CR-50 | 420-450 | Ms, mAb | MBL, D223-3 |
| H-221 | 3239-3460 | Rb, pAb | SCBT, sc-5578 |
| AF3820 | 1221-2661 | Gt, pAb | R&D, AF3820 |
| R4B | 1810-1825 | Ms, mAb | Jossen et al, 2007 |
| R5A | 1985-2058 | Ms, mAb | Jossen et al, 2007 |
| Ab12 | 3260-3428 | Ms, mAb | de Berkgeyck et al, 1998 |
| Ab14 | 3260-3428 | Ms, mAb | de Berkgeyck et al, 1998 |
| Ab17 | 3260-3428 | Ms, mAb | de Berkgeyck et al, 1998 |

FIG. 13C.

REELIN RESCUES COGNITIVE FUNCTION

CROSS REFERENCE TO RELATED APPLICATIONS

This application is a continuation of U.S. Nonprovisional application Ser. No. 13/206,174, filed on Aug. 9, 2011, which is a continuation of International Application, Serial Number PCT/US2010/023615 filed Feb. 9, 2010, which claims priority to U.S. Provisional Patent Application No. 61/150,890, filed Feb. 9, 2009; the contents of each of which are herein incorporated by reference.

GOVERNMENT INTEREST STATEMENT

This invention was made with Government support under Grant Number R01 NS043408 awarded by the National Institutes of Health. The Government has certain rights in the invention.

BACKGROUND OF THE INVENTION

The lipoprotein receptor signaling system is known to play a significant role in the adult CNS such as cholesterol homeostasis, clearance of extracellular proteins, modulating memory formation, synaptic transmission, plasticity and maturation through the activation of numerous signal transduction pathways. Importantly, the lipoprotein receptor ligand apolipoprotein E (apoE) is one of the best validated risk factors for late-onset, sporadic Alzheimer's disease (AD) (Hoe H S, Harris D C, Rebeck G W. Multiple pathways of apolipoprotein E signaling in primary neurons. *J Neurochem* 2005; 93:145-155; Hoe H S, Freeman J, Rebeck G W. Apolipoprotein E decreases tau kinases and phospho-tau levels in primary neurons. *Mol Neurodegener* 2006, 1:18; Hoe H S, Pocivaysek A, Chakraborty G, et al. Apolipoprotein E receptor 2 interactions with the N-methyl-Daspartate receptor. *J Biol Chem* 2006, 281:3425-3431). Moreover, the extracellular matrix protein reelin can bind to both lipoprotein receptors and amyloid precursor protein (APP) and is known to be associated with Aβ plaques in a number of AD mouse models (Chin J, Massaro C M, Palop J J, et al. Reelin depletion in the entorhinal cortex of human amyloid precursor protein transgenic mice and humans with Alzheimer's disease. *J Neurosci* 2007, 27:2727-2733; Hoareau C, Borrell V, Soriano E, Krebs M O, Prochiantz A, Allinquant B. Amyloid precursor protein cytoplasmic domain antagonizes reelin neurite outgrowth inhibition of hippocampal neurons. *Neurobiol Aging* 2008, 29:542-553; Hoe H S, Tran T S, Matsuoka Y, Howell B W, Rebeck G W. DAB1 and Reelin effects on amyloid precursor protein and ApoE receptor 2 trafficking and processing. J Biol Chem 2006, 281:35176-35185; and Miettinen R, Riedel A, Kalesnykas G, et al. Reelin-immunoreactivity in the hippocampal formation of 9-month-old wildtype mouse: effects of APP/PS1 genotype and ovariectomy. *J Chem Neuroanat* 2005, 30:105-1180). Aβ accumulation can influence reelin signaling and lipoprotein receptor function, thereby promoting AD pathogenesis and affecting synaptic and cognitive function.

Therefore, what is needed are specific agonists that act upon the lipoprotein receptor system in a manner similar to Reelin for use as therapeutics in the improvement of cognitive function as well as the treatment of neurological disease such as AD and other age-related neurodegenerative disorders.

SUMMARY OF INVENTION

The invention relates generally to methods of influencing, and enhancing, cognitive function by increasing, and/or preventing interference with, Reelin levels as well as the cellular signal transduction initiated or maintained with Reelin or Reelin signaling.

In a first embodiment, the invention includes a method of improving cognitive function, in a subject in need thereof, by administering a therapeutically effective amount of Reelin, a Reelin-specific modulator or an agonist of a lipoprotein receptor to the subject. The lipoprotein receptor can be selected from candidates such as ApoER2 and VLDLR. As disclosed herein, agonists or antagonists of the lipoprotein receptor for use with the inventive method include, but are not limited to, APC, Sep and Fc-RAP. In addition to administering exogenous Reelin, a Reelin-specific modulator, such as a recombinant Reelin fragment, can be used to increase Reelin levels and/or signaling. In an illustrative embodiment, the therapeutically effective amount of Reelin or an agonist of a lipoprotein receptor is approximately 5 nM.

In another embodiment, the invention includes a method of treating a symptom of a disease or disorder of the nervous system by administering a therapeutically effective amount of Reelin, a Reelin-specific modulator or an agonist of a lipoprotein receptor to a subject in need thereof. As with the previous embodiment, the lipoprotein receptor is selected from the group consisting of ApoER2 and VLDLR. The agonists of the lipoprotein receptor for use with the inventive method include, but are not limited to, APC, Sep and Fc-RAP. In this embodiment, the disease or disorder of the nervous system can be selected from the group consisting of fragile X syndrome, William's syndrome, Rett syndrome, Down's syndrome, Angelman syndrome, autism, ischemia, hypoxia, Alzheimer's disease, Reelin deficiency, schizophrenia, neurodegeneration, traumatic brain injury, mental retardation, dementia, and stroke. The therapeutically effective amount of Reelin or an agonist of a lipoprotein receptor is, in one example, approximately 5 nM.

A third embodiment of the invention includes a method of increasing dendritic spine density, in a subject in need thereof, by administering a therapeutically effective amount of Reelin, a Reelin-specific modulator or an agonist of a lipoprotein receptor to the subject. The lipoprotein receptor can be selected from candidates such as ApoER2 and VLDLR. As disclosed herein, agonists of the lipoprotein receptor for use with the inventive method include, but are not limited to, APC, Sep and Fc-RAP. In addition to administering exogenous Reelin, a Reelin-specific modulator, such as a recombinant Reelin fragment, can be used to increase Reelin levels and/or signaling. In an illustrative embodiment, the therapeutically effective amount of Reelin or an agonist of a lipoprotein receptor is about 5 nM.

BRIEF DESCRIPTION OF THE DRAWINGS

For a fuller understanding of the invention, reference should be made to the following detailed description, taken in connection with the accompanying drawings, in which:

FIG. 13C. Tri-epitope mapping. Antibodies that will be employed in the 3-epitope approach are listed.

Dendritic spines are reduced in the HRM compared to WT mice but after treatment with reelin, spine density is rescued. The last column of reelin represents the native in the concentration administered to the culture. Reelin was present up until 96 hours after introduction to culture and degradation did not begin until 72 hours.

Figure 15A:
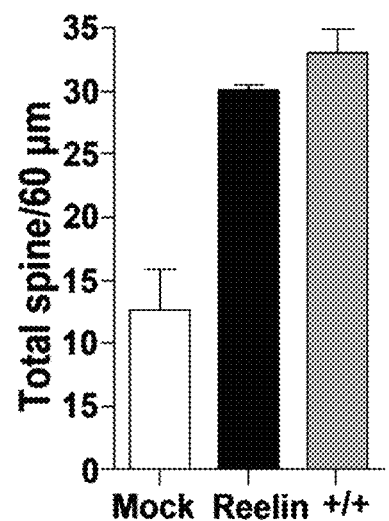
FIG. 15A. Reelin effects on dendritic spine density. Reelin was applied chronically to primary hippocampal neuronal cultures to examine its effect on dendritic spine density. Dendritic spines on a WT neuron are shown in an enlarged photo of a representative primary dendrite. The last column of reelin represents the native in the concentration administered to the culture. Reelin was present up until 96 hours after introduction to culture and degradation did not begin until 72 hours.
Figure 15B:
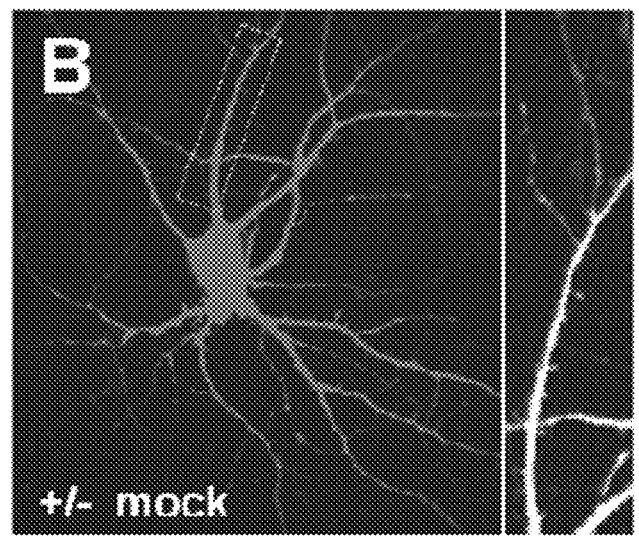
FIG. 15B. Reelin effects on dendritic spine density. Reelin was applied chronically to primary hippocampal neuronal cultures to examine its effect on dendritic spine density.
Figure 15C:
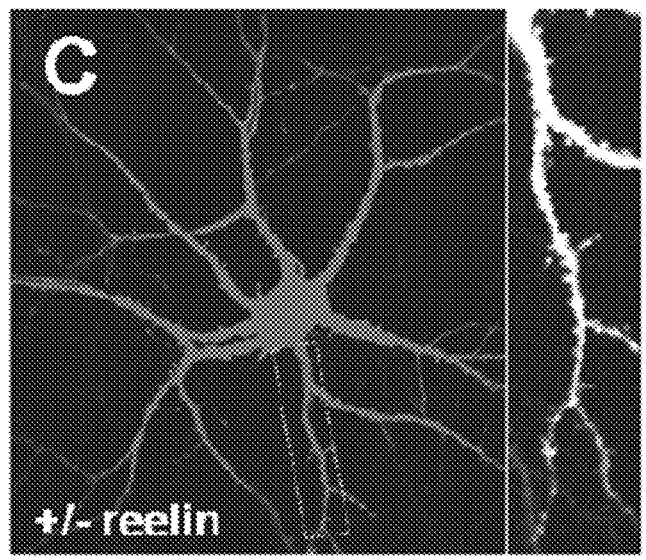

FIG. 15C. Reelin effects on dendritic spine density. Reelin was applied chronically to primary hippocampal neuronal cultures to examine its effect on dendritic spine density. Dendritic spines are reduced in the HRM compared to WT mice but after treatment with reelin, spine density is rescued. The last column of reelin represents the native in the concentration administered to the culture. Reelin was present up until 96 hours after introduction to culture and degradation did not begin until 72 hours.

Figure 15D:
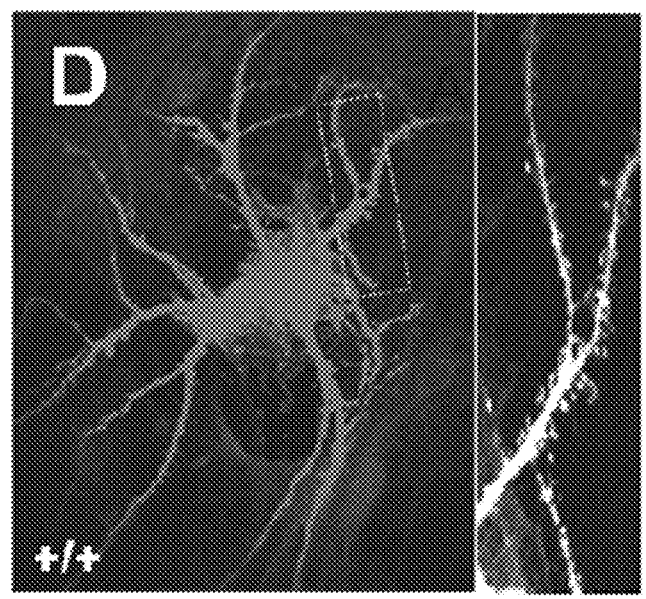

FIG. 15D. Reelin effects on dendritic spine density. Reelin was applied chronically to primary hippocampal neuronal cultures to examine its effect on dendritic spine density. Dendritic spines are very sparse in the knockout reelin mice but after treatment with reelin, spine density deficits are rescued. The last column of reelin represents the native in the concentration administered to the culture. Reelin was present up until 96 hours after introduction to culture and degradation did not begin until 72 hours.

Figure 15E:
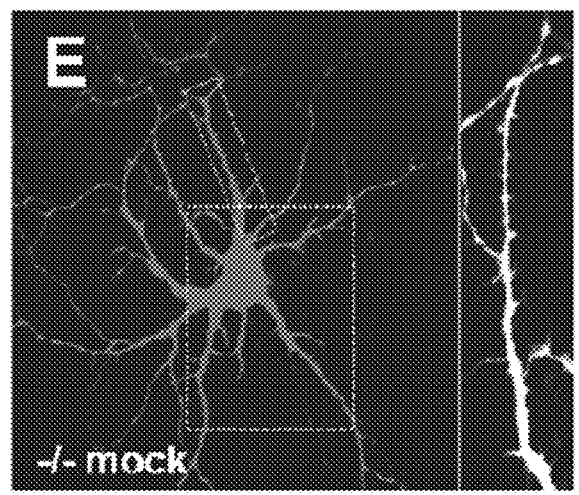

FIG. 15E. Reelin effects on dendritic spine density. Reelin was applied chronically to primary hippocampal neuronal cultures to examine its effect on dendritic spine density. Dendritic spines are very sparse in the knockout reelin mice but after treatment with reelin, spine density deficits are rescued. The last column of reelin represents the native in the concentration administered to the culture. Reelin was present up until 96 hours after introduction to culture and degradation did not begin until 72 hours.

Figure 15F:
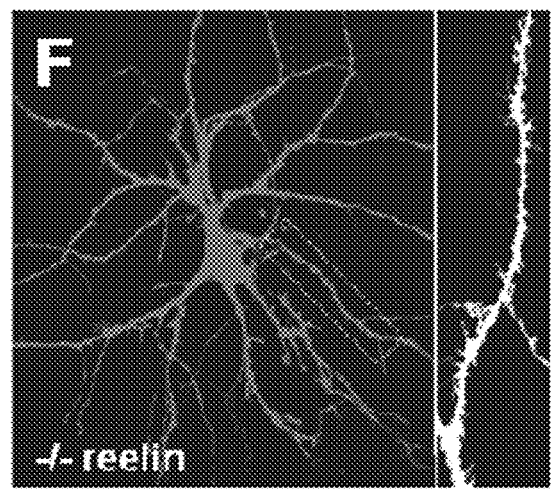

FIG. 15F. Reelin effects on dendritic spine density. Reelin was applied chronically to primary hippocampal neuronal cultures to examine its effect on dendritic spine density. Dendritic spines were quantified using a confocal microscope. Dendritic spines were defined as any protrusion from a primary dendrite excluding any secondary dendrites. Dendritic spines were counted and measured every 50 um of the dendrite. There is a significant increase in spines in reelin-treated cells (n=3) versus mock-treated cells (n=3). The last column of reelin represents the native in the concentration administered to the culture. Reelin was present up until 96 hours after introduction to culture and degradation did not begin until 72 hours.

Figure 15G:
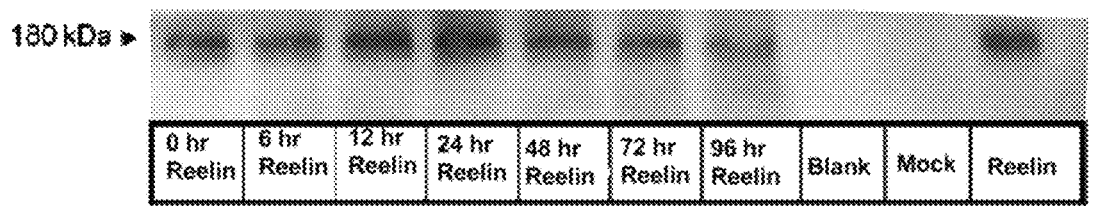

FIG. 15G. Reelin effects on dendritic spine density. Reelin was applied chronically to primary hippocampal neuronal cultures to examine its effect on dendritic spine density. Reelin levels in culture were determined by a Western Blot. Samples were taken out of culture at 0, 6, 12, 24, 48, 72, and 96 hrs to determine the levels of reelin degradation in vitro. The last column of reelin represents the native in the concentration administered to the culture. Reelin was present up until 96 hours after introduction to culture and degradation did not begin until 72 hours.

Figure 16A:
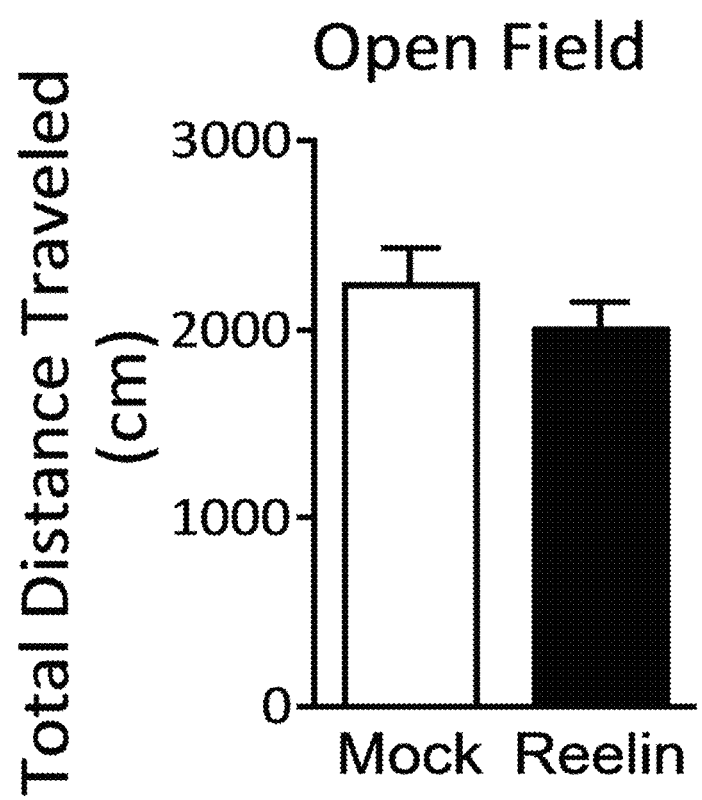

FIG. 16A. Locomotor activity, nociception and anxiety are unaltered by drug treatments. Open field behavior utilized to evaluate locomotor activity. The total distance traveled during the 15 min test was similar for the three conditions (mock HRM n=13, reelin HRM n=13, Rap WT n=10; ANOVA p=0.23).

Figure 16B:
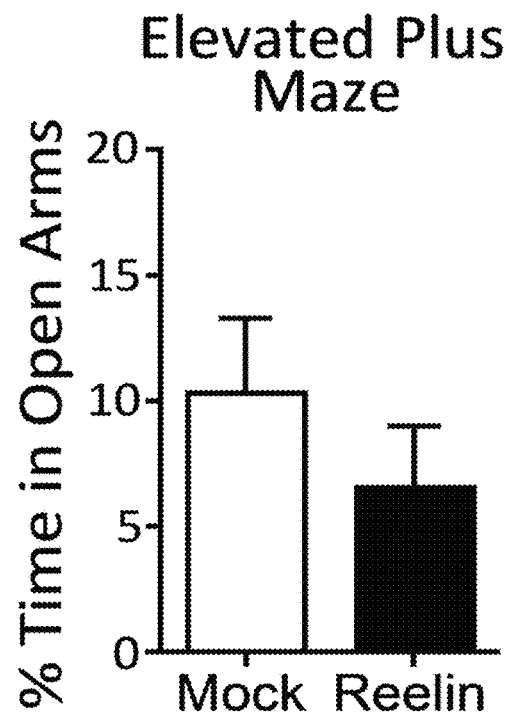

FIG. 16B. Locomotor activity, nociception and anxiety are unaltered by drug treatments. Elevated Plus Maze utilized to determine anxiety. The percent of time spent in the open arms were similar for the three conditions (mock HRM n=11, reelin HRM n=10, Rap WT n=13; percent time ANOVA p=0.49 and open arm entries ANOVA p=0.63).

Figure 16C:
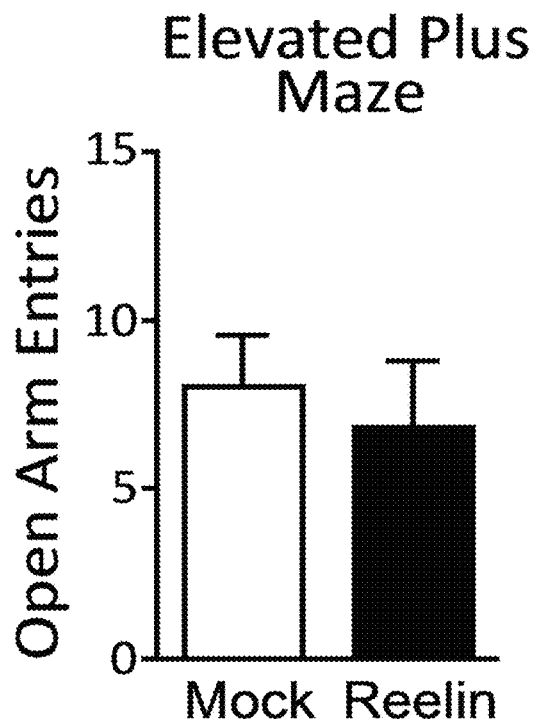

FIG. 16C. Locomotor activity, nociception and anxiety are unaltered by drug treatments. Elevated Plus Maze utilized to determine anxiety. The number of open arm entries were similar for the three conditions (mock HRM n=11, reelin HRM n=10, Rap WT n=13; percent time ANOVA p=0.49 and open arm entries ANOVA p=0.63).

Figure 16D:
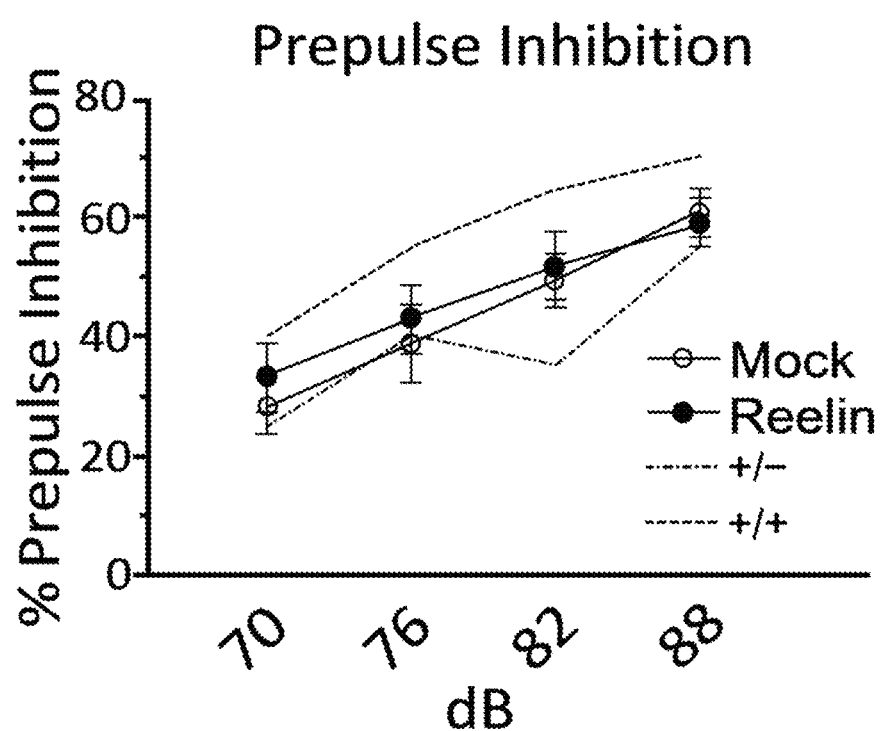

FIG. 16D. Locomotor activity, nociception and anxiety are unaltered by drug treatments. Prepulse inhibition utilized to evaluate startle response. The startle response to a 120 dB acoustic stimulation is similar for the three conditions (mock HRM n=14, reelin HRM n=16, Rap WT n=15; ANOVA p=0.56). Results from Qiu et al. (2005) are depicted with dashed lines for reference.

Figure 16E:
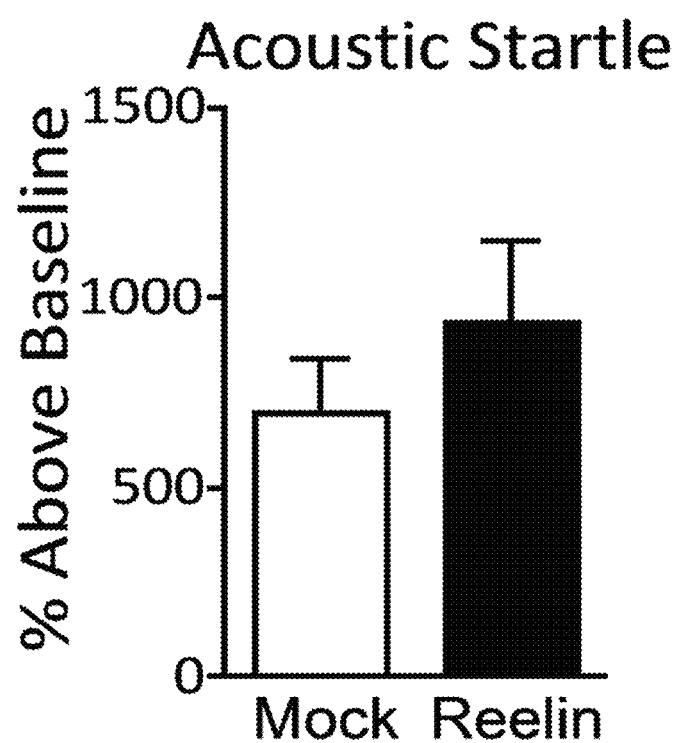

FIG. 16E. Locomotor activity, nociception and anxiety are unaltered by drug treatments. Acoustic startle utilized to evaluate startle response. The startle response to a 120 dB acoustic stimulation is similar for the three conditions (mock HRM n=14, reelin HRM n=16, Rap WT n=15; ANOVA p=0.56). Results from Qiu et al. (2005) are depicted with dashed lines for reference.

Figure 17A:
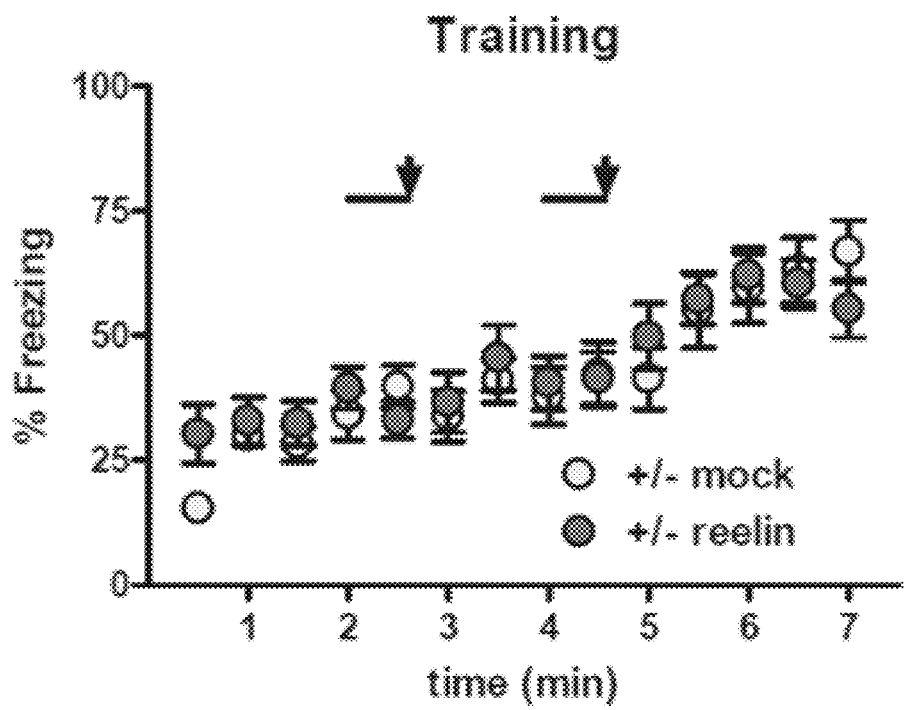

FIG. 17A. HRM contextual fear conditioning deficits are rescued by application of exogenous reelin. Freezing during the conditioning paradigm was similar for both conditions (mock HRM n=16, reelin HRM n=16). The tone is represented by the black bar and the shock by the black arrows. Freezing during reintroduction to the conditioning context.

Figure 17B:
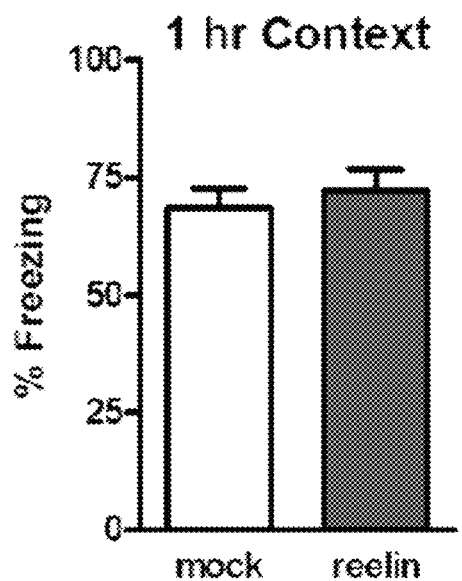

FIG. 17B. HRM contextual fear conditioning deficits are rescued by application of exogenous reelin. Freezing was similar for the three conditions 1 hr post conditioning (mock HRM n=13, reelin HRM n=13).

Figure 17C:
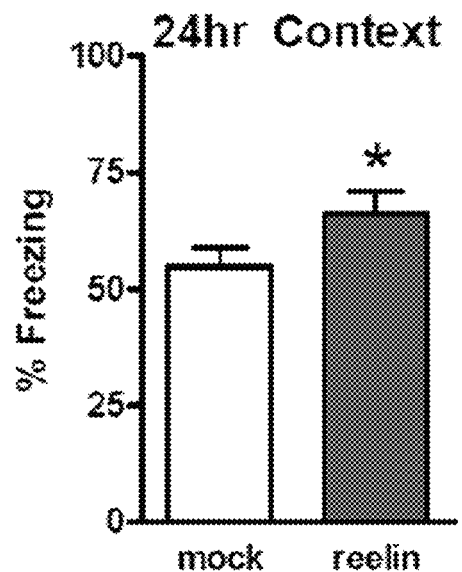

FIG. 17C. HRM contextual fear conditioning deficits are rescued by application of exogenous reelin. Reelin-treated HRM freezing was significantly greater than mock-treated HRM 24 hrs post conditioning (mock HRM n=16, reelin HRM n=16; t-test p=0.02).

Figure 17D:
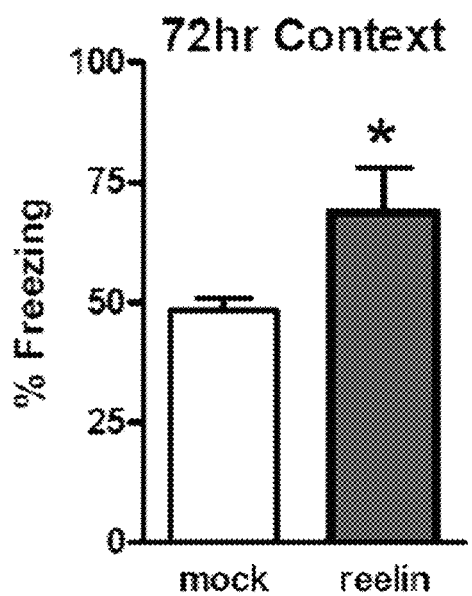

FIG. 17D. HRM contextual fear conditioning deficits are rescued by application of exogenous reelin. Reelin-treated HRM freezing was significantly greater than mock-treated HRM 72 hrs post conditioning (mock HRM n=5, reelin HRM n=4; t-test p=0.026).

Figure 17E:
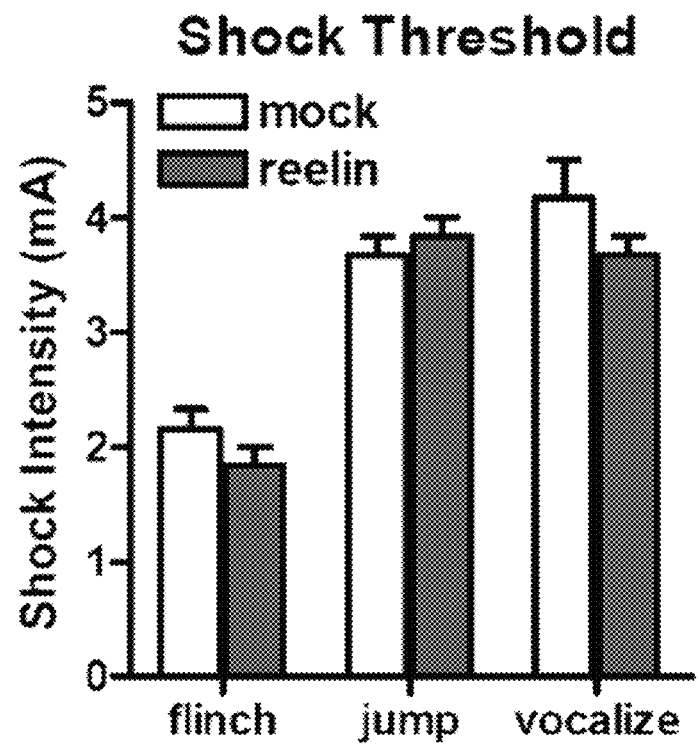

FIG. 17E. HRM contextual fear conditioning deficits are rescued by application of exogenous reelin. Shock threshold analysis to evaluate nociception. The shock intensity in which mice flinched, jumped, or vocalized was similar for both conditions (mock HRM n=3, reelin HRM n=3; ANOVA p=0.22).

Figure 18A:
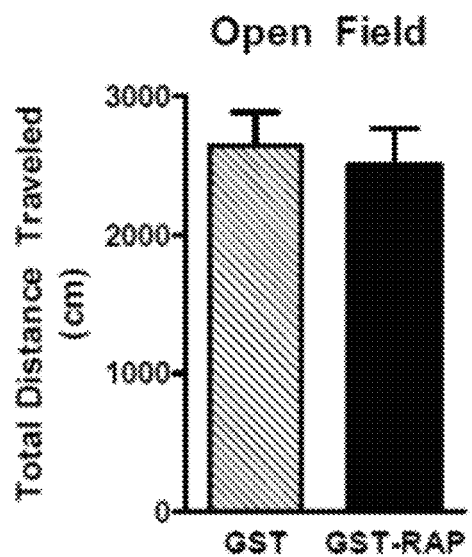

FIG. 18A. Locomotor activity, nociception and anxiety are unaltered by drug treatments. Open field behavior utilized to evaluate locomotor activity. The total distance traveled during the 15 min test was similar for the two conditions (Rap WT n=10).

Figure 18B:
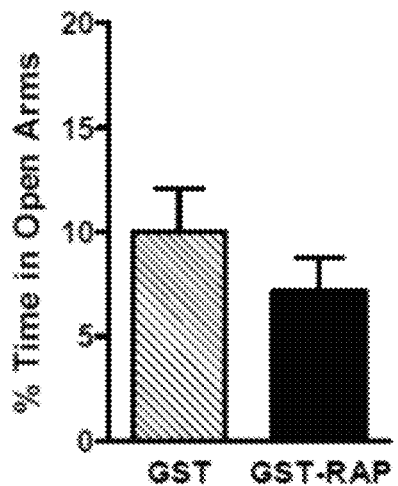

FIG. 18B. Locomotor activity, nociception and anxiety are unaltered by drug treatments. Elevated Plus Maze utilized to determine anxiety. The percent of time spent in the open arms were similar for both conditions (Rap WT n=13; percent time ANOVA p=0.49 and open arm entries ANOVA p=0.63).

Figure 18C:
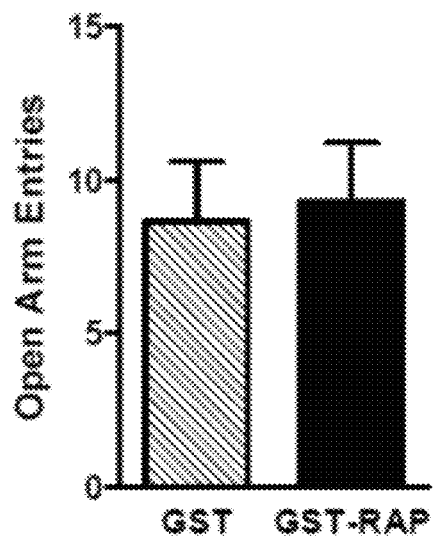

FIG. 18C. Locomotor activity, nociception and anxiety are unaltered by drug treatments. Elevated Plus Maze utilized to determine anxiety. The number of open arm entries were similar for both conditions (Rap WT n=13; percent time ANOVA p=0.49 and open arm entries ANOVA p=0.63).

Figure 18D:
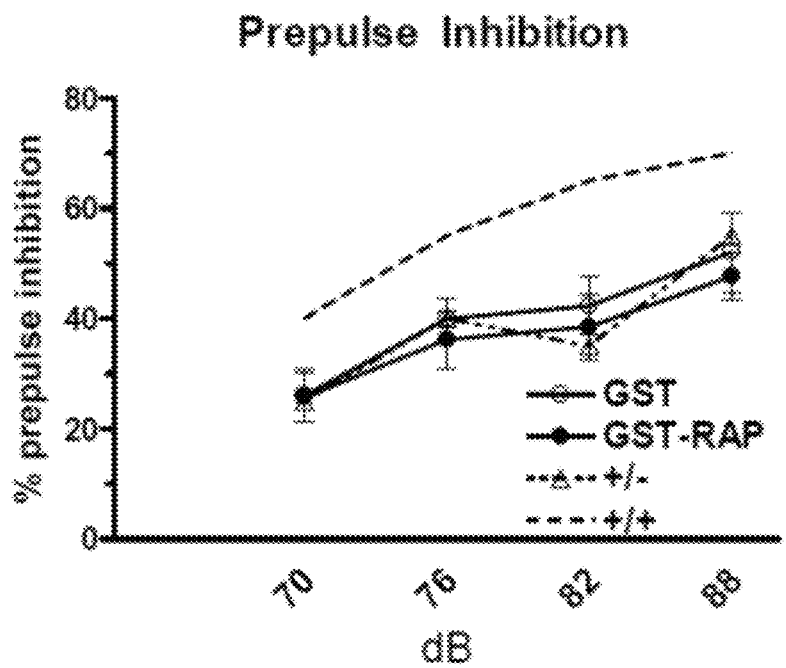

FIG. 18D. Locomotor activity, nociception and anxiety are unaltered by drug treatments. Prepulse inhibition, Results from Qiu et al. (2005) are depicted with dashed lines for reference.

Figure 18E:
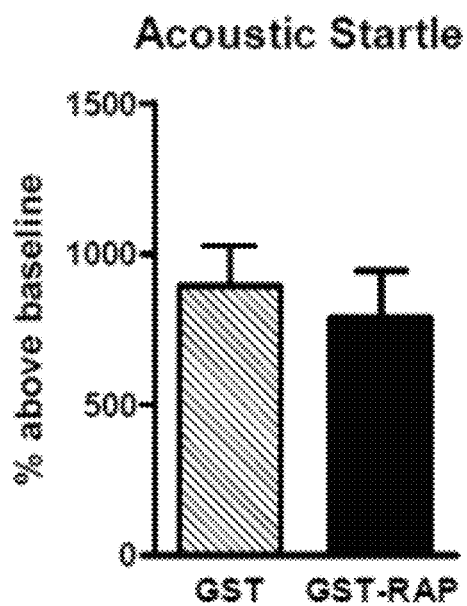

FIG. 18E. Locomotor activity, nociception and anxiety are unaltered by drug treatments. Acoustic startle utilized to evaluate startle response. The startle response to a 120 dB acoustic stimulation is similar for both conditions (Rap WT n=15; ANOVA p=0.56).

Figure 19A:
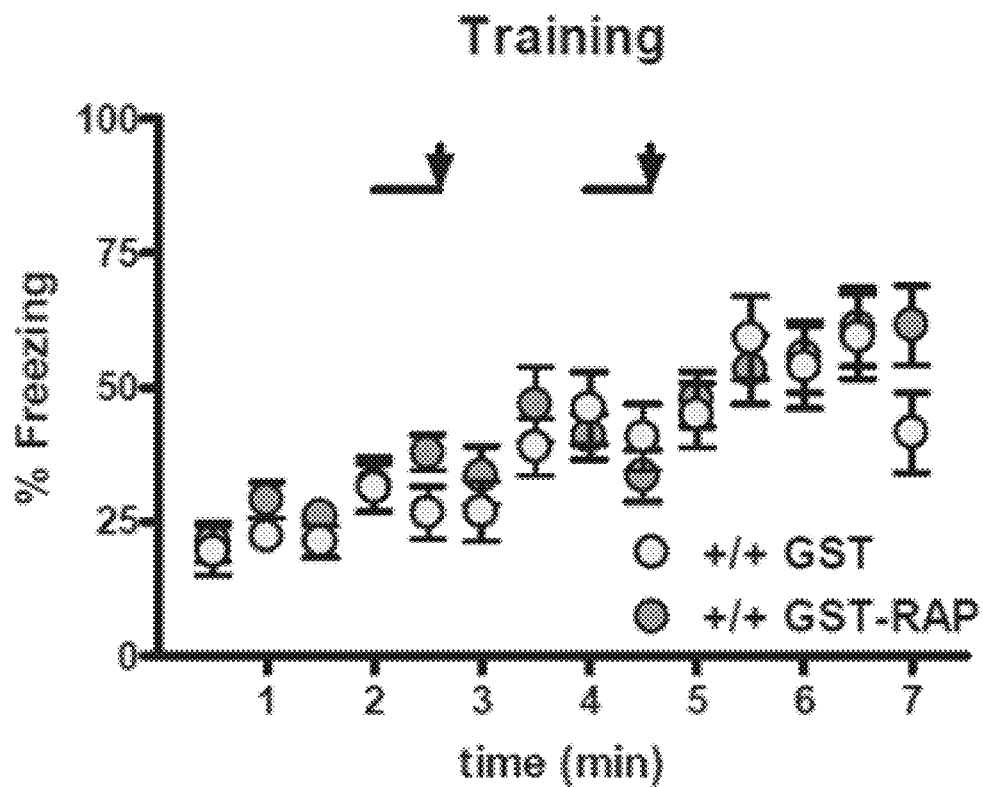

FIG. 19A. Freezing during the conditioning paradigm was similar for both conditions (Rap WT n=13). The tone is represented by the black bar and the shock by the black arrows. Freezing during reintroduction to the conditioning context.

Figure 19B:
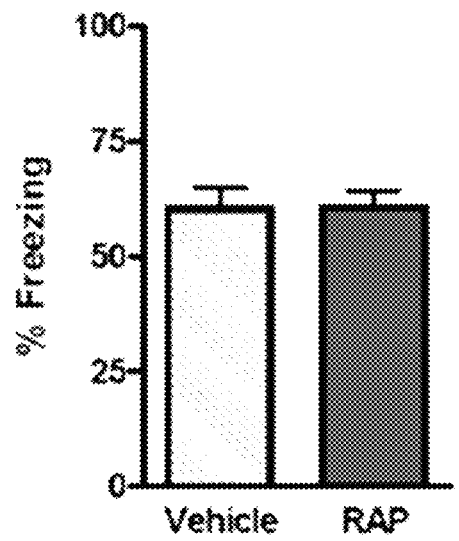

FIG. 19B. Freezing was similar for both conditions 1 hr post conditioning (Rap WT n=9).

Figure 19C:
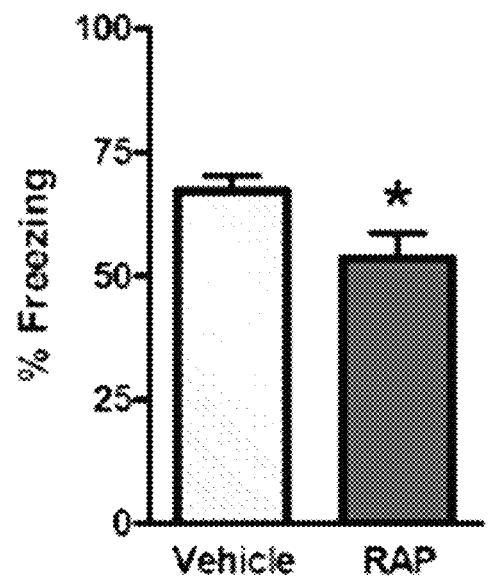

FIG. 19C. RAP-treated WT freezing was significantly less than vehicle-treated WT (Rap WT n=13) 24 hrs post conditioning There was no difference between mock-treated HRM freezing and Rap-treated WT freezing at any time tested (See FIGS. 15B-C).

Figure 19D:
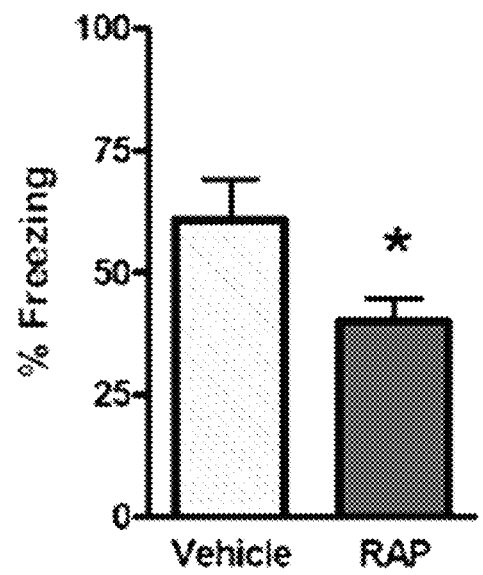

FIG. 19D. Freezing was similar for both conditions 1 hr post conditioning (Rap WT n=9). (C) RAP-treated WT freezing was significantly less than vehicle-treated WT (Rap WT n=13) 72 hrs post (Rap WT n=6). There was no difference between mock-treated HRM freezing and Rap-treated WT freezing at any time tested (See FIGS. 15B-C).

Figure 19E:
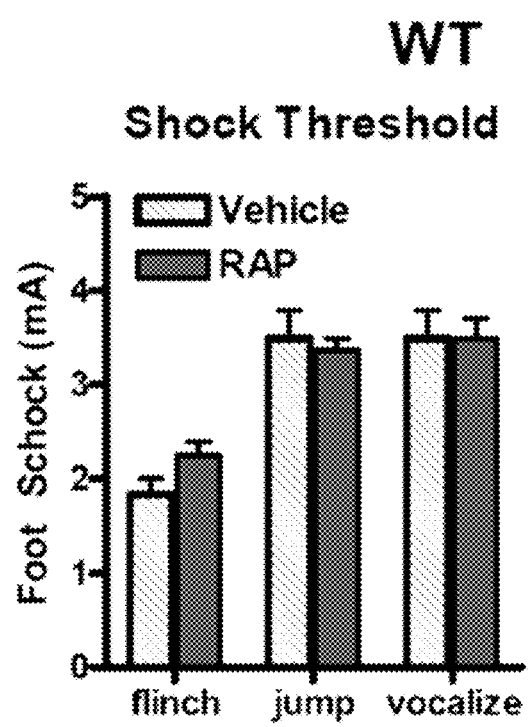

FIG. 19E. Shock threshold analysis to evaluate nociception. The shock intensity in which mice flinched, jumped, or vocalized was similar for both conditions (Rap WT n=4; ANOVA p=0.22).

DETAILED DESCRIPTION OF THE PREFERRED EMBODIMENT

Recent research has established a role for lipoprotein receptors in cognitive processes and implicated this receptor family in the pathological processes that underlie the progression of AD. Two of the major ligands for these receptors, apoE and reelin, appear to have signaling capabilities that can significantly impact synaptic function, directly interact with APP and modulate its metabolism, and are sensitive to Aβ accumulation. Aβ accumulation disrupts lipoprotein receptor signaling, resulting in concomitant disruption of cognitive function. Furthermore, interference of reelin and/or lipoprotein receptor signaling results in aberrant APP metabolism and Aβ clearance that in turn exacerbates Aβ accumulation and plaque deposition. Therefore, increased reelin signaling through direct reelin application or usage of other lipoprotein receptor agonists can be used to mitigate Aβ-dependent cognitive disruption and progression of plaque pathology.

Reelin: In the adult hippocampus, the glycoprotein Reelin is expressed by interneurons residing primarily in the hilar region of dentate gyrus, and the stratum lacunosum-moleculare layer of the hippocampus proper. Reelin-expressing cells can also be found in stratum oriens and stratum radiatum of area CA1 and CA3 and is associated with pyramidal cells of the hippocampus. Induction of long-term potentiation (LTP), a form of synaptic plasticity that results in a lasting increase in synaptic efficacy, requires NMDAR (NMDARs) activation and the subsequent up-regulation of AMPA receptor expression and function. Changes in AMPA receptors (AMPARs) can be achieved either by increased subunit phosphorylation or by increased subunit synthesis and trafficking to the specific synaptic sites. In contrast, NMDARs serve as coincidence detectors and play a major role in the induction of synaptic plasticity. The opening of NMDAR ion channels requires both glutamate binding and post-synaptic membrane depolarization. Some NMDAR subunits, such as NR1, NR2A and NR2B are also subjected to modulatory phosphorylation at serine/threonine or tyrosine residues. Phosphorylation of NMDAR subunits modulates both channel kinetics and trafficking to synaptic sites. It follows that if reelin were important for modulation of synaptic plasticity, then NMDARs and AMPARs would be logical targets given their importance in induction and expression of synaptic plasticity.

APC: Activated protein C (APC) is a serine protease that possesses both anticoagulant and cytoprotective properties that are currently being exploited for the treatment of conditions such as sepsis, stroke and multiple sclerosis. The anticoagulant properties of APC are achieved through the protein C (PC) pathway, while its cryoprotective effects are orchestrated through PAR1 (protease activated receptor; and PAR3, endothelial PC receptor (EPCR) and ApoER2. In mice, APC has been found to protect against diabetic endothelial and glomerular injury, multiple sclerosis and ischemia/reperfusion injury in the kidney and lung.

APC has already been approved by the U.S. Food and Drug Administration for use in adult severe sepsis and is currently in Phase I/IIa clinical trials for the treatment of ischemic stroke (National Institutes of Health, Activated Protein C in Acute Stroke Trial (APCAST), 2010). Numerous groups have also recently developed APC variants that possess less anticoagulant activity, which has proven to limit APC's clinical efficacy. Specifically, a mutant designated 3K3A-APC has 80% reduced anticoagulant activity but retains normal PAR1 and EPCR-dependent anti-apoptotic activity. Relevant to the use of APC to treat neuropathologies, APC and APC variants have been found to effectively cross the BBB via EPC-mediated transport.

Recently, APC has been found to activate the Reelin signaling cascade via high affinity ligation to ApoER2. Specifically, APC-treated monocytes demonstrated increased active Dab1 (Tyr220-p), Akt Ser473-p, and GSK3beta Ser9-p levels. Pre-treatment with RAP or knocking down of ApoER2 were found to attenuate these effects, while inhibitors of EPCR and PAR1 had no effect. Interestingly, APC was found to bind to ApoER2 with 30 nM affinity, but not to soluble VLDLR. To relate APC's effects to ApoER2 signaling, RAP was found to block APC-mediated inhibition of endotoxin-induced tissue factor pro-coagulant activity of U937 cells.

Recent work has highlighted the importance of Reelin signaling in normal learning and memory (Weeber E J, Beffert U, Jones C, et al. Reelin and ApoE receptors cooperate to enhance hippocampal synaptic plasticity and learning. *J Biol Chem* 2002, 277:39944-39952), as well as pathological instances where this signaling is perturbed. APC is now a candidate modulator of Reelin signaling, as it appears to have the structural moieties to bind to ApoER2 and activate downstream effectors. It is of immense scientific and clinical relevance that APC modulation of Reelin signaling be tested, as it could yield novel therapeutic avenues.

SePP1: Approximately 60% of selenium in plasma is present in selenoprotein P. This protein differs from other selenoproteins in that it incorporates up to 10 Se atoms per molecule in the form of selenocysteine as opposed to single selenocysteines. Selenoprotein P is abundant throughout the body, suggesting that one function is to serve as a primary transporter in systemic selenium delivery. This is especially evident in the CNS where selenoprotein P levels can be maintained independent of plasma selenium. However, genetic ablation of selenoprotein P results in reduced, but not a commensurate decrease in CNS-associated selenium levels, suggesting that other selenium proteins compensate for the selenoprotein P deficiency and supporting the hypothesis that basal selenium levels are essential for the brain and have a priority for systemically available selenium. Sepp1 (−/−) mice fed a selenium-deficient diet show severe motor dysfunction associated and associated neuronal degeneration, which can be prevented by supplementation with high dietary selenium.

Reduced dietary selenium can have significant effects on levels of selenoproteins involved in oxidative stress and their related effects on glutathione peroxidases, thioredoxin reductases and methionine sulfoxide reductases. Selenium, through incorporation into selenoproteins, provides protection from reactive oxygen species (ROS)-induced cell damage. This is interesting in light of the role of oxidative stress and subsequent production of ROS in neurodegenerative disorders such as Alzheimer's disease, Parkinson's disease and Duchenne muscular dystrophy. The inventors have previously examined the consequences of selenoprotein P deficiency on cognitive capacity and synaptic function with a focus on the hippocampus, an area of the CNS intimately involved in learning and memory processes. Sepp1 (−/−) mice demonstrated no overt behavioral phenotype, but were found to have a subtle disruption in acquisition of spatial learning and memory. In contrast, synaptic transmission was altered and short- and long-term synaptic plasticity was severely disrupted in area CA1 of hippocampus. Interestingly, the inventors found that when Sepp1 (+/+) mice were fed a low Selenium diet (0 mg/kg), they too exhibited altered synaptic transmission and synaptic plasticity. Our observations suggest an important role for both selenoprotein P and dietary selenium in overall proper synaptic function.

Fc-RAP: Reelin molecules have recently been discovered to form higher-order complexes in vitro and in vivo. This observation was further refined by showing that reelin is secreted in vivo as a disulfide-linked homodimer. Deletion of a short region, called the CR-50 epitope, located at the N-terminus of the molecule abolishes oligomerization. This mutated reelin fails to efficiently induce Dab1 phosphorylation in primary mouse neurons.

These results are in accordance with earlier observations that an antibody against the CR-50 epitope antagonizes reelin function in vitro and in vivo. Clustering of ApoER2 and/or VLDLR induces Dab1 phosphorylation and downstream events including activation of SFKs and modulation of PKB/Akt. Furthermore, modulation of long-term potentiation (LTP), one of the biological effects of reelin, is also mimicked by reelin-independent receptor clustering. These findings strongly suggest that receptor-induced dimerization or oligomerization is sufficient for Dab1 tyrosine phosphorylation and downstream signaling events without the need for an additional co-receptor providing tyrosine kinase activity.

As shown herein, Reelin plays an active role in the processes of synaptic plasticity and learning. The invention also includes the identification and use of mechanisms for Reelin protein processing to enhance and/or repair cognitive function. For example, it is disclosed herein that: contextual fear learning and theta burst stimulation (tb-stim) cause changes in Reelin processing; the metalloproteinases, tPA and MMP-9 are differentially involved in Reelin processing during synaptic plasticity and learning; supplementation of Reelin fragment complement can enhance associative and spatial learning and memory; and reelin fragments associate with Aβ plaques, its expression and processing is altered by AD-related mutations, and Reelin supplementation can overcome the LTP deficits found in the Tg2576 AD mouse model.

Reelin-Induced Enhancement of Long-Term Potentiation in Acute Hippocampal Slices.

Figure 1:
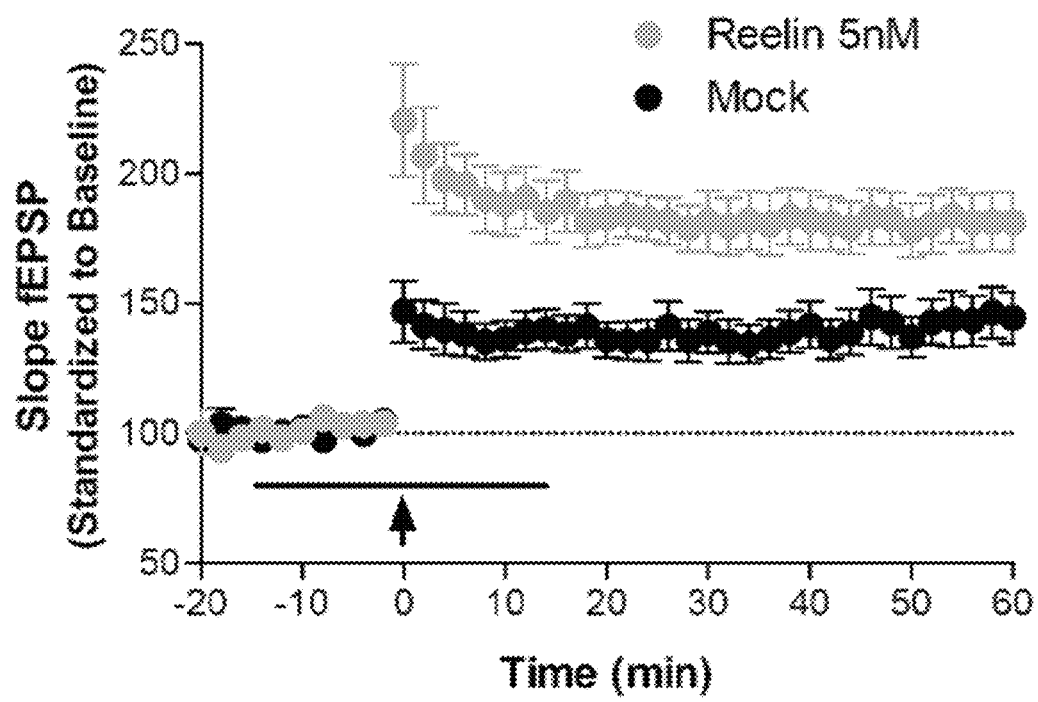
FIG. 1. Application of recombinant Reelin enhances LTP. Field recordings from acute hippocampal slices in area CA1. Wild-type mice were perfused with either 5 nM reelin (n=7) or Mock (n=6).

Reelin is a naturally occurring, secreted protein produced by interneurons of the hippocampus and cortex. Knockout (KO) mice of both reelin receptors, ApoER2 and VLDLR show deficits in long-term potentiation (LTP) in the stratum radiatum of the hippocampus. To verify the absence of reelin signaling underlies this deficit, the inventors performed a simple experiment consisting of the perfusion of purified reelin protein onto wild-type hippocampal slices. As shown in FIG. 1, reelin application enhanced HFS-LTP induced in the stratum radiatum.

Post-Synaptic Mechanisms of Reelin Enhancement of NMDAR Currents.

Reelin also demonstrates the ability to potentiate CA1 glutamatergic responses. The inventors have recently shown that ApoER2 is present post-synaptically and forms a functional complex with NMDARs in CA1 (4). The derivation of mEPSCNMDA is illustrated in FIG. 2. Cells treated with mock had miniature excitatory post-synaptic current due to NMDA receptors (mEPSCNMDA) that were not significantly changed compared with that before mock treatment ($p>0.05$). Treatment with Reelin was found to significantly increase mEPSCNMDA amplitude ($p<0.001$).

Figure 2A:
FIG. 2A. Reelin enhances NMDAR currents through postsynaptic mechanisms. Illustration of measurement of EPSCNMDA.
Figure 2A:
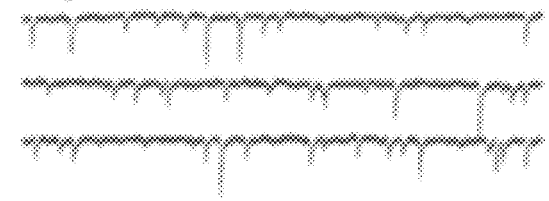
Figure 2B:
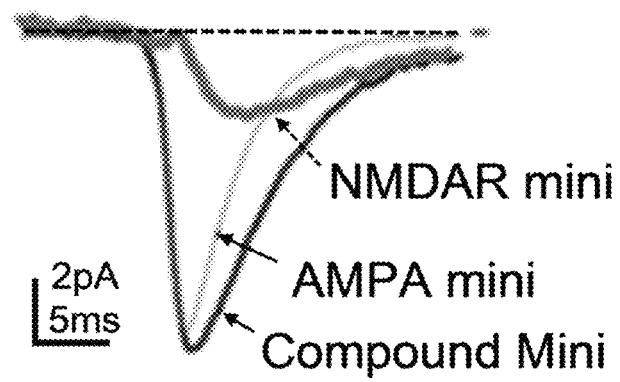
FIG. 2B. Reelin enhances NMDAR currents through postsynaptic mechanisms. Illustration of measurement of EPSCNMDA. The thick gray trace represents the mEPSC-NMDA.
Figure 2C:
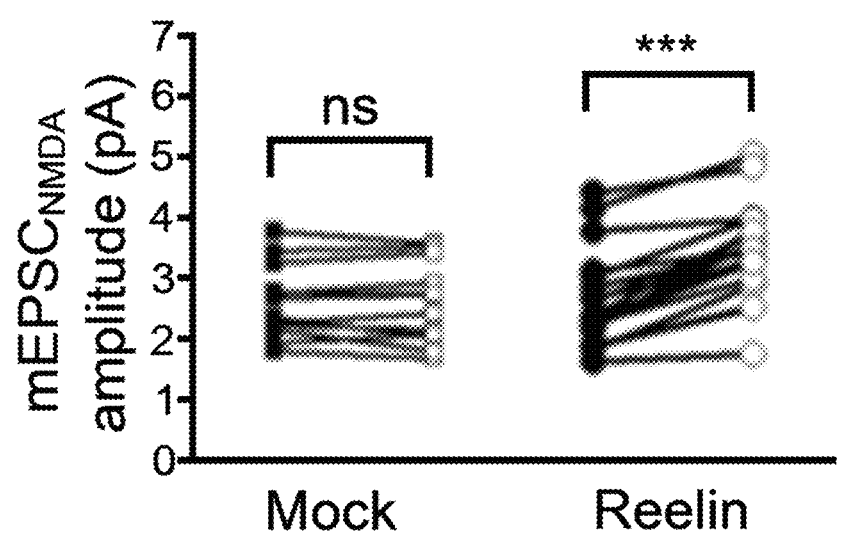
FIG. 2C. Reelin enhances NMDAR currents through postsynaptic mechanisms. Reelin treatment significantly increased mEPSCNMDA amplitude (closed circle, before reelin; open circle, after reelin; ***p<0.001; n=18; paired t test). Treatment with mock was without effect [closed square, before mock; open square, after mock; not significant (ns), p>0.05; n=13; paired t test].
Figure 2D:
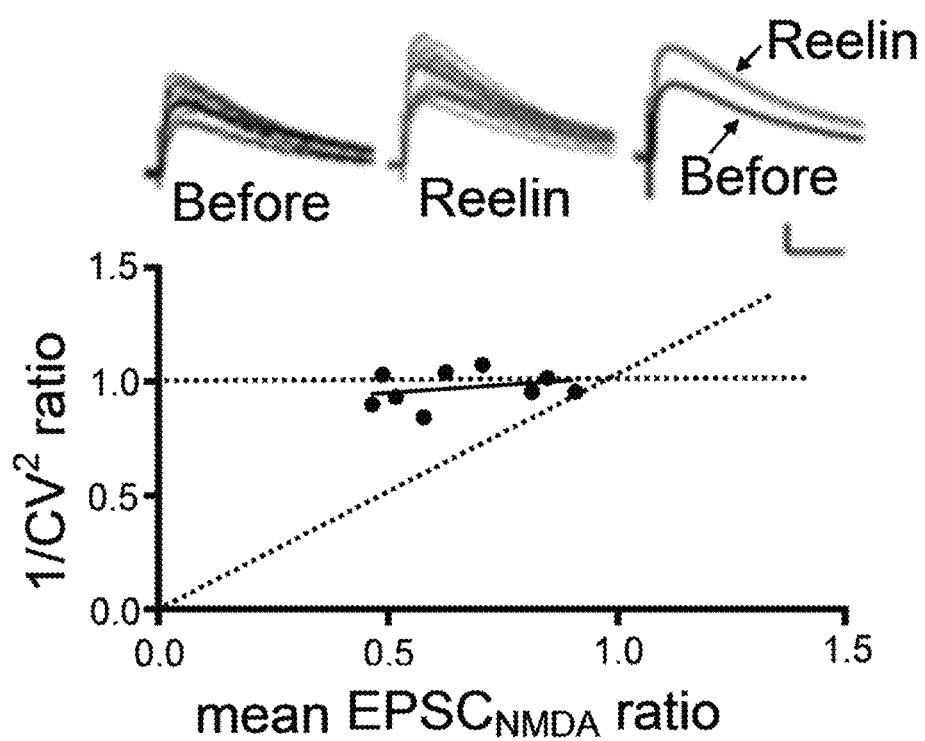
FIG. 2D. Reelin enhances NMDAR currents through postsynaptic mechanisms. No correlation of 1/CV2 ratios and mean EPSCNMDA ratios (after/before reelin) was revealed based on recordings from nine cells (r=0.31; p=0.4; Spearman's test).

To further verify that synaptic NMDAR response was increased as a result of postsynaptic effects of Reelin, the inventors analyzed the coefficient of variation (CV) of synaptically-evoked NMDAR whole-cell current. When $1/CV^2$ ratios were plotted versus mean EPSCNMDA ratios before and after a 30 minute reelin application in nine experiments, no correlation was established (FIG. 2D). However, the $1/CV^2$ ratios remain relatively unchanged across varying mean EPSCNMDA ratios, confirming reelin activation through a postsynaptic mechanism in CA1 to enhance NMDAR activity.

Differential Effects of Reelin Treatment on Surface Levels of AMPAR and NMDAR subunits.

Chronic Reelin treatment can result in the increased AMPA component of synaptic response, alteration of EPSC-NMDA kinetics and ifenprodil sensitivity. The inventors sought to determine whether the protein expression levels of AMPAR and NMDAR subunits were changed by Reelin in CA1. Both total and surface levels of GluR1, NR1, NR2A, and NR2B were probed by Western blotting. The inventors first examined whether GluR1, an AMPAR subunit that is increasingly expressed during developmental maturation and subjected to regulate trafficking during synaptic plasticity, was increased on CA1 cell surfaces.

Figure 3A:
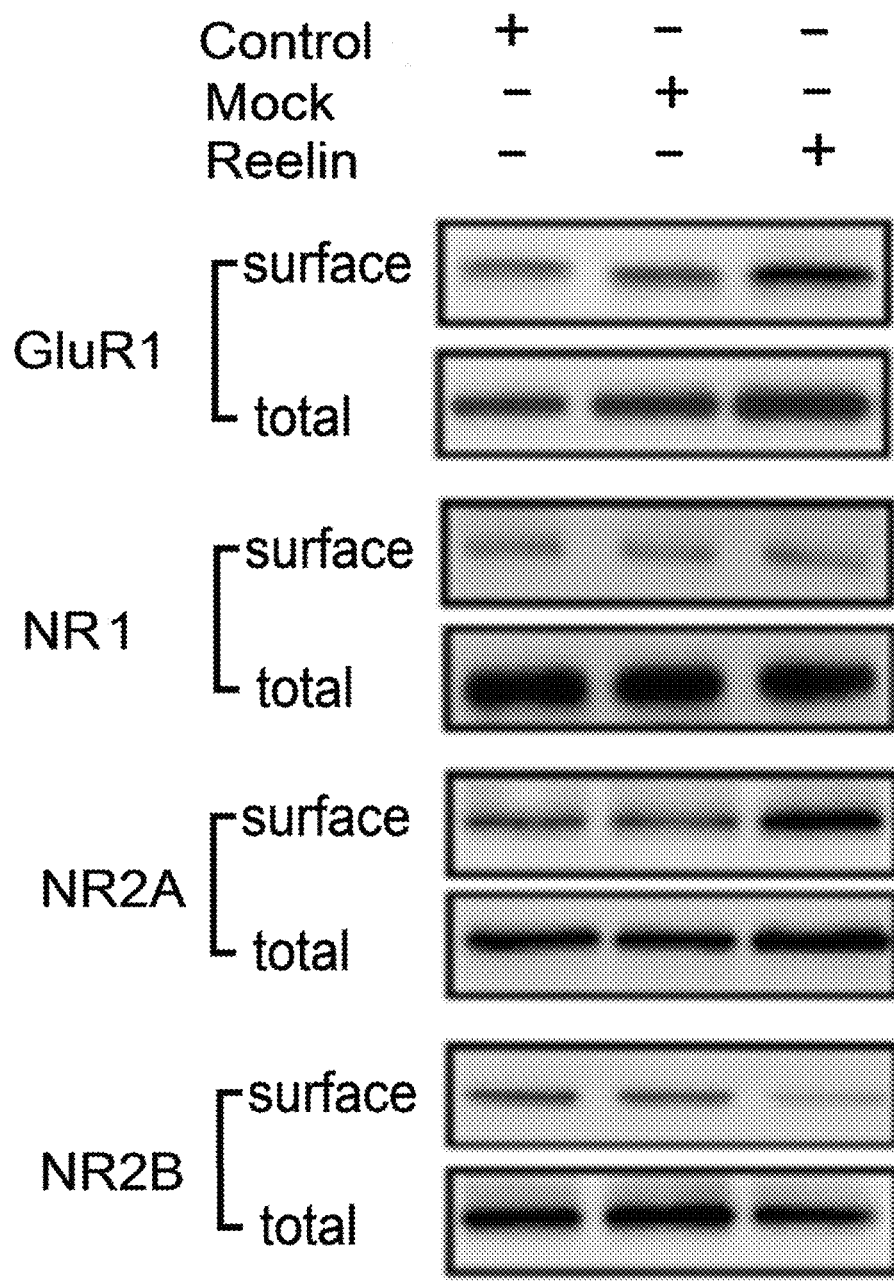
FIG. 3A. Reelin signaling alters surface expression and total levels of glutamate receptor subunits. Representative blots showing levels of both surface and total GluR1, NR1, NR2A, and NR2B.
Figure 3B:
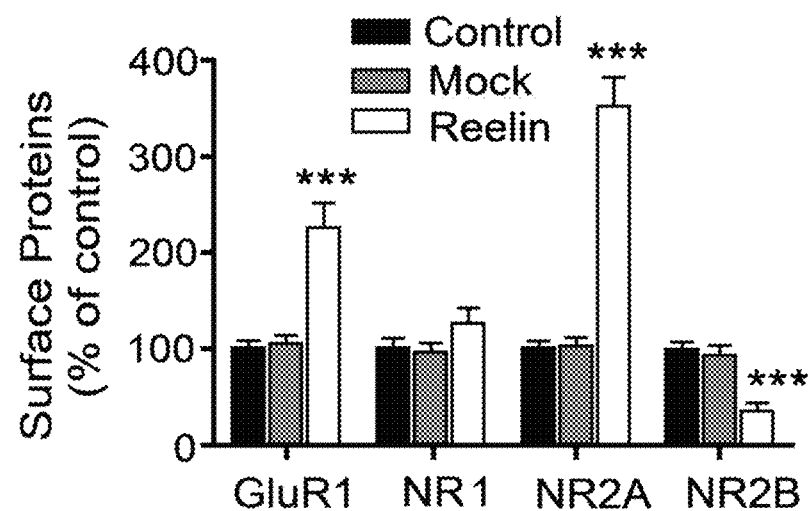
FIG. 3B. Reelin signaling alters surface expression and total levels of glutamate receptor subunits.) Quantitative results of surface glutamate receptor subunits pooled from 4 experiments. Compared with mock groups, both surface GluR1 and NR2A were significantly increased [GluR1, $F(2,11)=15.56$, *P<0.001; NR2A, $F(2,11)=44.9$, *P<0.001], and the level of surface NR2B was significantly reduced [$F(2,11)=22.6$, ***P<0.001] after chronic Reelin treatment.
Figure 3C:
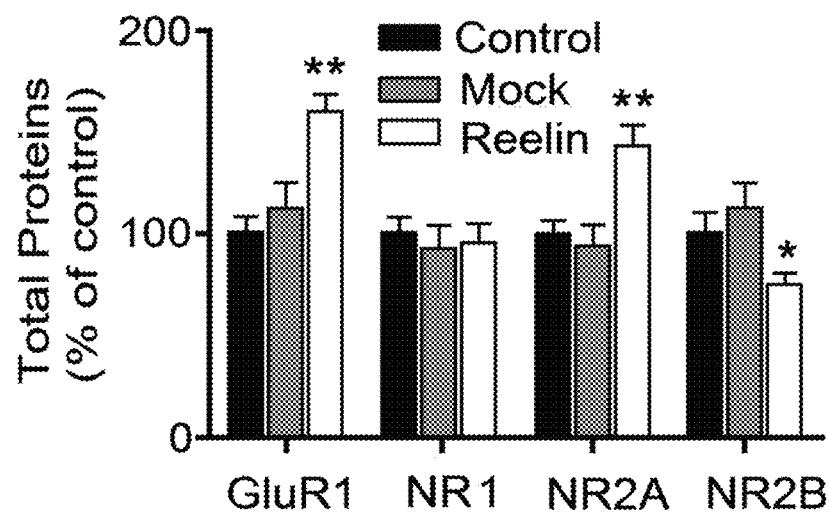
FIG. 3C. Reelin signaling alters surface expression and total levels of glutamate receptor subunits. Reelin treatment significantly increased levels of total GluR1 [$F(2,11)=11.2$, P<0.01], NR2A [$F(2,14)=9.75$, P<0.01], and decreased level of total NR2B [$F(2,11)=4.1$, *P<0.05]. In contrast, neither total nor surface (in 3B) levels of NR1 was observed.

FIG. 3 shows that reelin treatment significantly increased levels of surface GluR1 compared with mock-treated groups, indicating regulated expression and surface insertion via increased $mEPSC_{AMPA}$ and AMPA/NMDA current ratio after chronic Reelin treatment. No changes of either surface or total NR1 levels were observed. In comparison, both total and surface NR2A expression levels were significantly increased after reelin treatment versus mock treatment. Moreover, both total and surface NR2B protein levels were significantly decreased following reelin treatment. Mock treatment had no effect on different glutamate receptor subunit levels compared with non-treated control groups.

Reelin signaling translates from a role in synaptic plasticity to learning and memory.

Reelin heterozygotes show deficits in both synaptic plasticity and cognitive function. An approximate 50% reduction of Reelin expression results in deficits in both synaptic plasticity and cognitive function (Qiu, S., K. M. Korwek, A. R. Pratt-Davis, M. Peters, M. Y. Bergman, and E. J. Weeber. 2006. Cognitive disruption and altered hippocampus synaptic function in Reelin haploinsufficient mice. *Neurobiol Learn Mem* 85:228-242). Furthermore, bilateral infusion of the lipoprotein antagonist RAP (receptor associated protein), which effectively blocks Reelin binding to its receptors dramatically, reduced associative learning (FIGS. 4A-4D). These results demonstrate a requirement for Reelin for normal memory formation and raise the interesting question of whether increasing Reelin signaling can enhance memory.

Figure 4A:
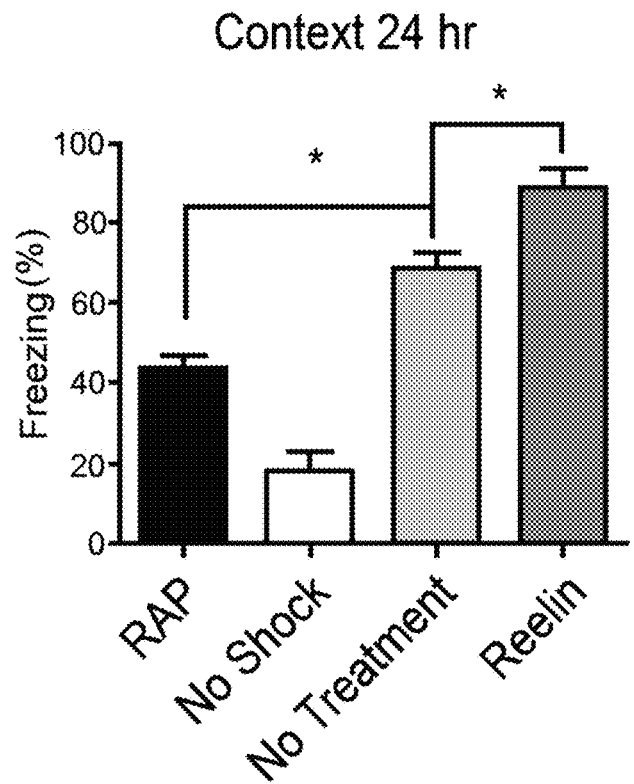
FIG. 4A. Reelin supplementation can improve associative learning and spatial learning. Wild type mice were given either 5 nM RAP or 5 nM Reelin by bilateral injection into the ventricles 3 hours prior to receiving fear conditioning. 24 hrs after training, mice were placed into the context and freezing measured. RAP was found to inhibit learning and memory while Reelin led to an enhancement (RAP n=9, no shock n=5, no treatment n=7, Reelin n=5; p>0.05).

The effect of Reelin deficiency on synaptic function is contrasted when Reelin concentrations are enhanced. Direct bilateral ventricle infusion of recombinant Reelin fragment compliment 3 hours prior to associative fear conditioning training enhanced memory formation when tested 24 hours after training in 3-4 month-old wild-type mice (FIG. 4A).

Figure 4B:
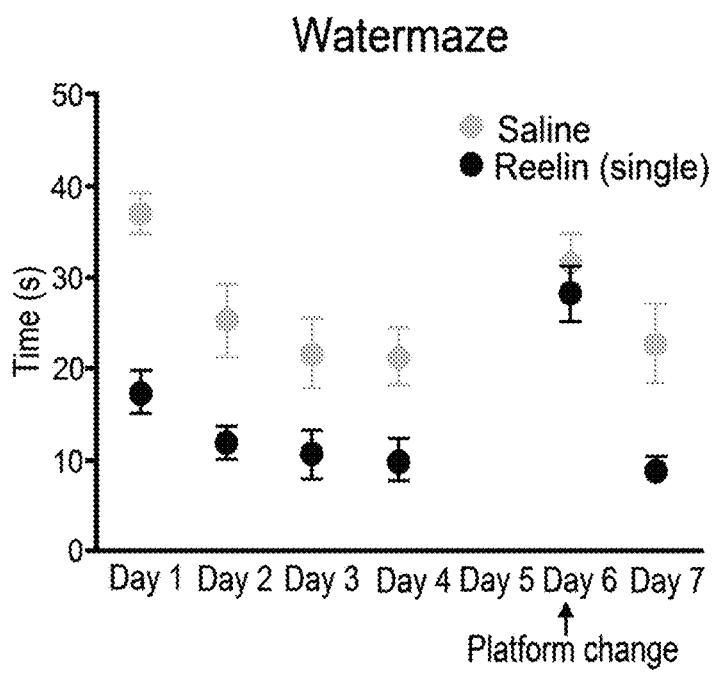
FIG. 4B. Reelin supplementation can improve associative learning and spatial learning. Wild type mice were trained to find a hidden platform through the Morris Water maze. Mice were given a single injection of either 5 nM Reelin (red circle, n=4) or Vehicle (open circle, n=6). On day 5, a probe trial was given then the mice were trained to find a new platform location on day 6.
Figure 4C:
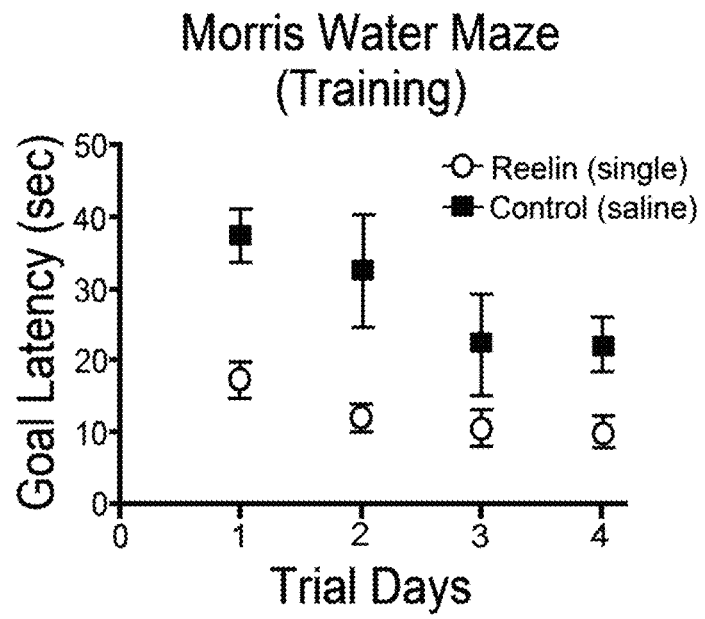
FIG. 4C. Reelin supplementation can improve associative learning and spatial learning. Examination of latencies from individual trials on day 1. (*=p>0.05).
Figure 4D:
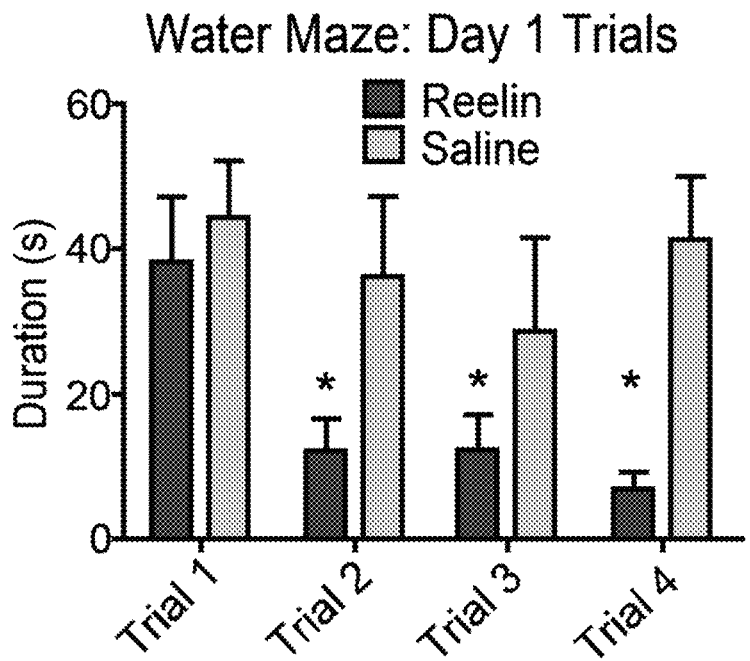
FIG. 4D. Reelin supplementation can improve associative learning and spatial learning. Wild type mice were trained to find a hidden platform through the Morris Water maze. Mice were given a single injection of either 5 nM Reelin (n=4) or Vehicle (n=6).

Furthermore, a single injection of Reelin into the ventricles improved spatial learning in the hidden platform water maze (FIG. 4B). Mice that were retrained to find a different platform location (opposite) on day 6 continued to show increased learning ability compared to saline injected mice. Mice receiving a single Reelin injection 5 days prior to training show a lower latency to find the platform on day one. A closer examination shows that the latency to find the platform is significantly reduced after a single exposure to the training paradigm (FIG. 4C). Mice that were retrained to find a different platform location continued to show differences between reelin and saline injections. Swim speeds and all other measurements of activity between treated and non-treated animals remained the same. This data dramatically illustrate the ability of Reelin to modulate in vivo learning and memory formation and the importance of research aimed to identify the mechanisms controlling Reelin protein processing and how the fragments subsequently modulate cognitive function.

Reelin Supplementation Overcame Aβ-Dependent Changes in Synaptic Plasticity.

Figure 5A:
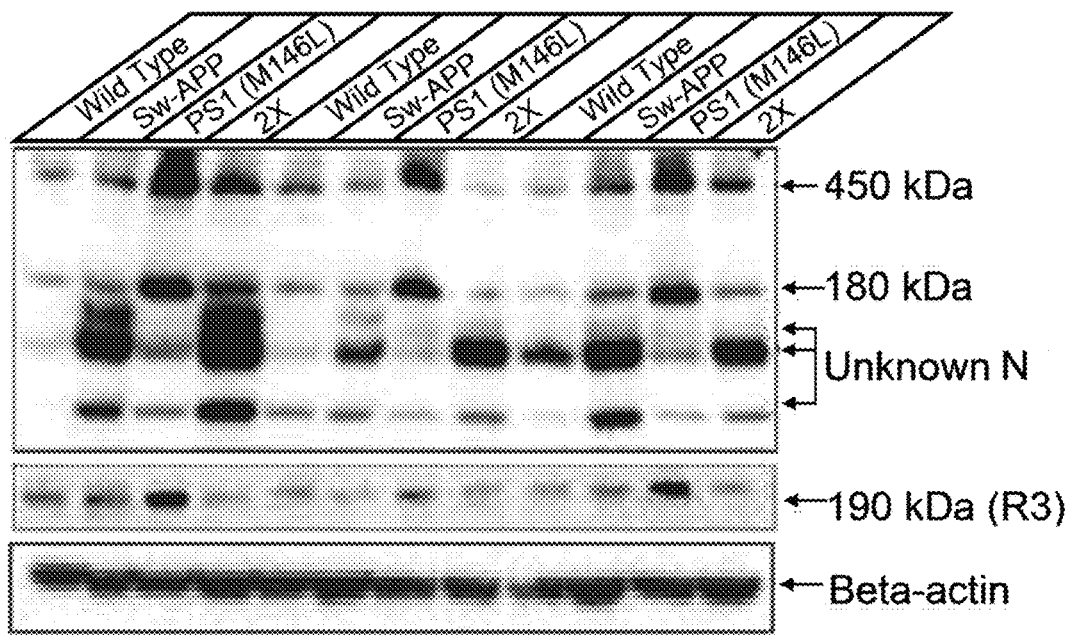
FIG. 5A. Reelin signaling is altered in AD mouse models. Isolated cortices from 14-month old wild type, Tg2576 (SweAPP), PS1-FAD (M146L), and 2x (SweAPP×M146L) were subjected to western analysis (n=4). No significant differences were detected in Reelin 450, 190 and 180 kDa products in Tg2576 versus wild type, but unidentified N-terminal species recognized by G10 were significantly elevated in Tg2576 and 2x mice. In contrast, Reelin 450 and 180 kDa products were significantly elevated in PS1-FAD and 2x mice (p<0.05).
Figure 5B:
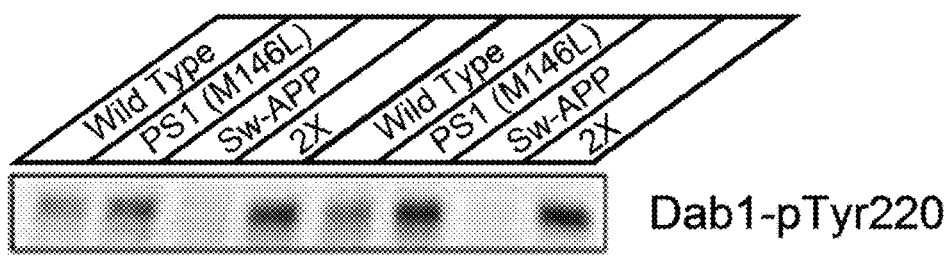
FIG. 5B. Reelin signaling is altered in AD mouse models. There were significant reductions in Dab1-pTyr220 in Tg2576 mice, and significant elevations in both PS1-FAD and 2x mice.

Reelin signaling is involved in a variety of physiologic changes to the excitatory synapse, as well as normal mammalian cognitive function. Reelin metabolism is altered in three mouse models for AD (PS1-FAD, SweAPPxPS1, and Tg2576) (FIG. 5A). These changes in Reelin fragment complement appear to be correlated with alterations in downstream Reelin signaling, as phosphorylation of the major downstream component, Dab-1, is increased in the SweAPPXPS1 and PS1-FAD, and significantly decreased in the single SweAPP (Tg2576) mouse (FIG. 5B). These data suggest that Reelin metabolism is particularly sensitive to changes in APP processing and/or Aβ accumulation.

Figure 5C:
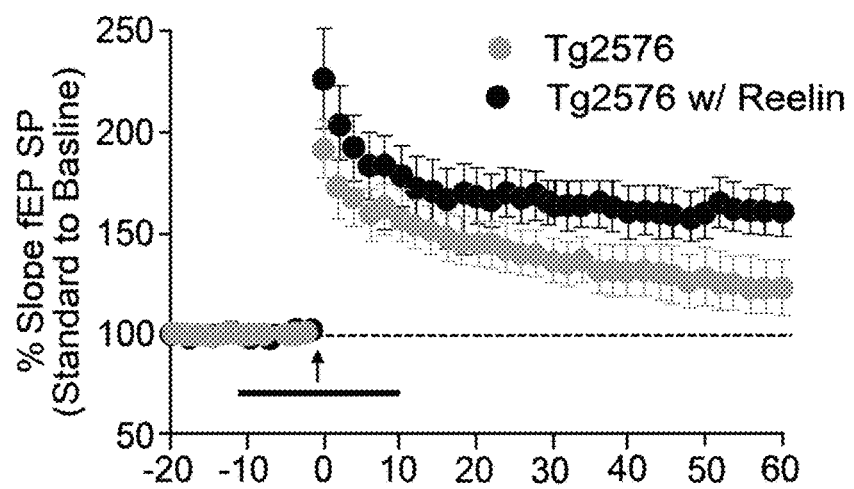
FIG. 5C. Reelin signaling is altered in AD mouse models. Application of Reelin (5 nM) prior to stimulation was able to rescue deficits in HFS-stimulated LTP in area CA1 of Tg2576 mice.
Figure 5D:
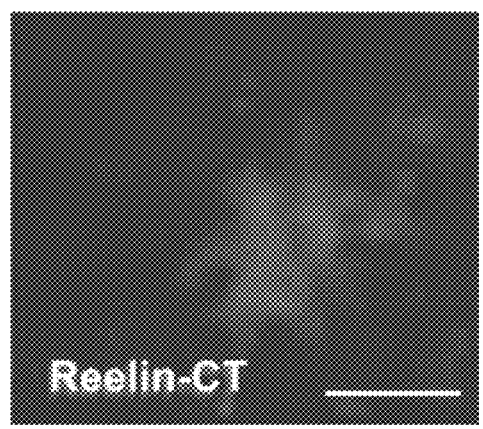
FIG. 5D. Reelin signaling is altered in AD mouse models. The 3-epitope strategy for mapping Reelin processing in vivo was employed on 14-month old Tg2576 horizontal sections. Reelin-CT (G20). Scale bar=15 μm.
Figure 5E:
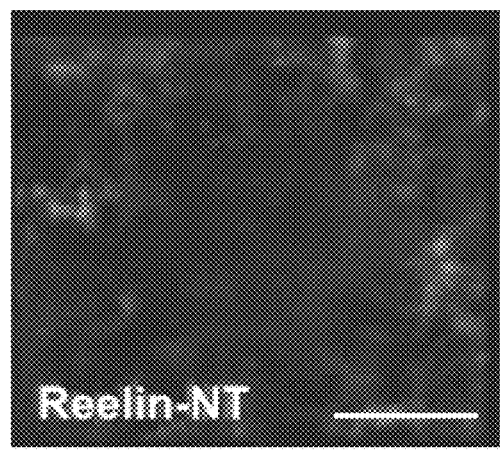
FIG. 5E. Reelin signaling is altered in AD mouse models. The 3-epitope strategy for mapping Reelin processing in vivo was employed on 14-month old Tg2576 horizontal sections. Reelin-NT. Scale bar=15 μm.
Figure 5F:
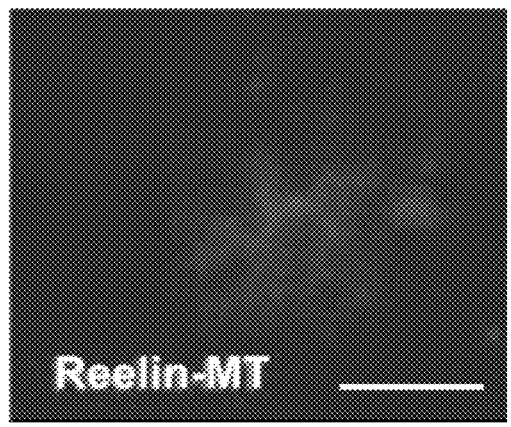
FIG. 5F. Reelin signaling is altered in AD mouse models. The 3-epitope strategy for mapping Reelin processing in vivo was employed on 14-month old Tg2576 horizontal sections. Reelin-MT (AF3820), detected Reelin fragments containing R7-8 and R3-6, respectively, sequestered at the core of a dense-core plaque detected with 6E10 (anti-Aβ). Scale bar=15 μm.
Figure 5G:
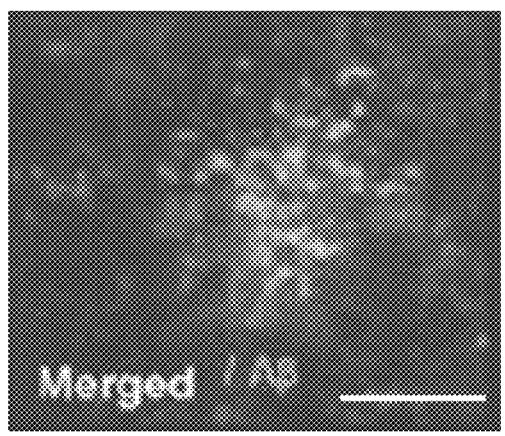
FIG. 5G. Reelin signaling is altered in AD mouse models. The 3-epitope strategy for mapping Reelin processing in vivo was employed on 14-month old Tg2576 horizontal sections. Reelin-CT (G20), -NT, -MT (AF3820) were merged, detecting Reelin fragments containing R7-8 and R3-6, respectively, sequestered at the core of a dense-core plaque detected with 6E10 (anti-Aβ). Scale bar=15 μm.
Figure 5H:
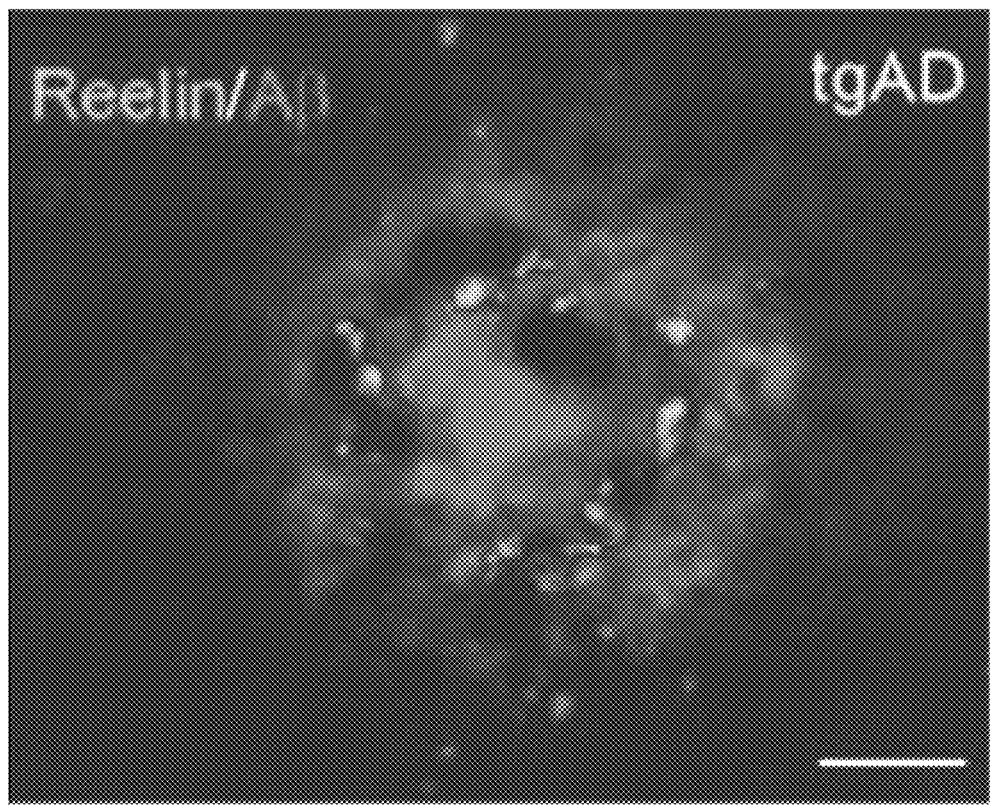
FIG. 5H. Reelin signaling is altered in AD mouse models. The 3-epitope strategy for mapping Reelin processing in vivo was employed on 14-month old Tg2576 horizontal sections. Reelin-NT fragments (N-R2) surrounded the plaque core in the tg2576 mouse model. Scale bar=15 μm.
Figure 6:
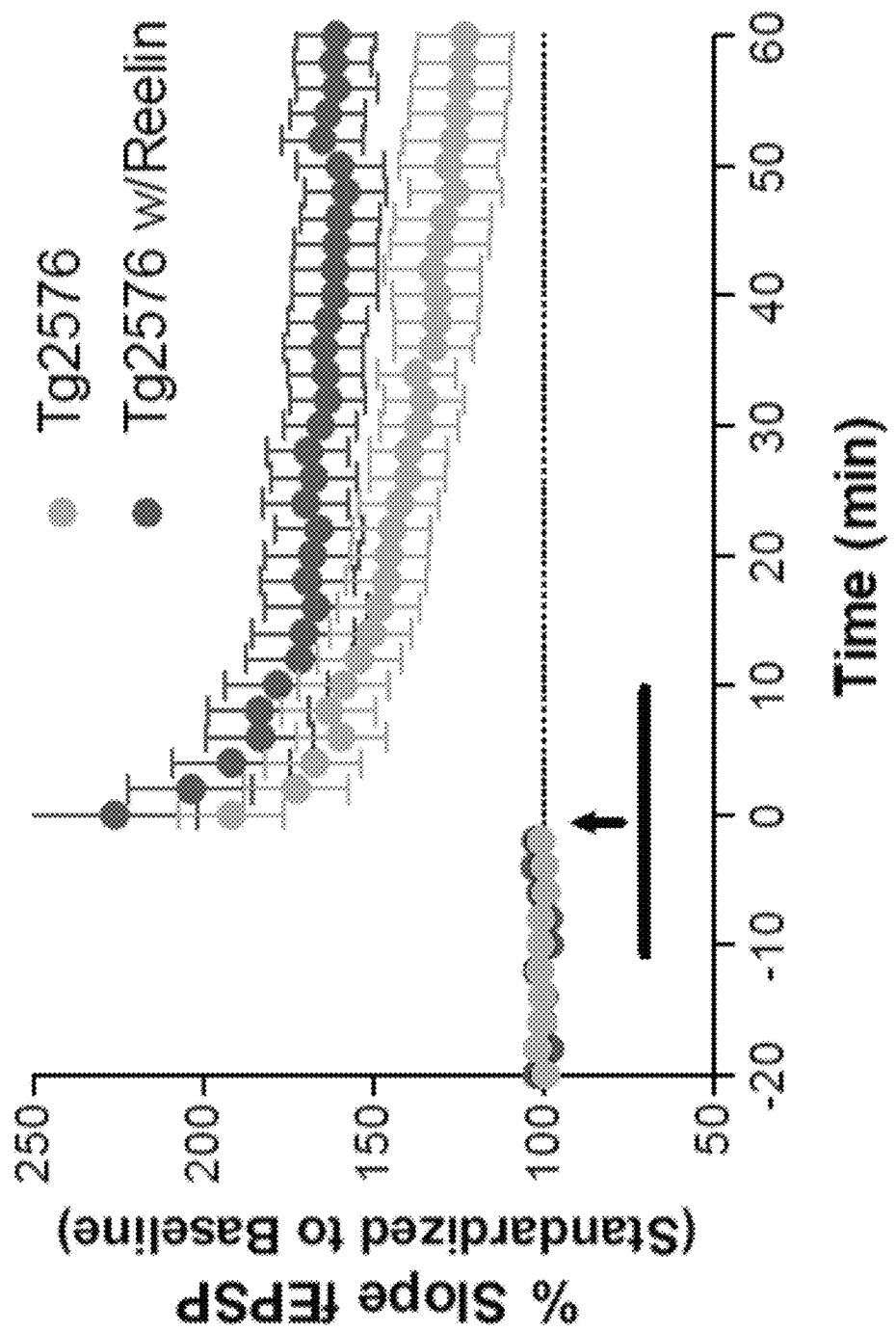
FIG. 6. LTP induction using a standard 2-train, 100 Hz HFS was given to hippocampal slices from 12 month-old Tg2576 mice. A set of slices were perfused with 5 nM reelin. Reelin treated slices showed an increase of LTP induction to that of wild-type levels.

The alteration in Reelin fragment complement and Dab-1 phosphorylation in the Tg2576 mice may represent a compromised Reelin signaling system, a phenomenon that if true could be responsible for the synaptic plasticity deficits reported in these mice (Mitchell, J. C., B. B. Ariff, D. M. Yates, K. F. Lau, M. S. Perkinton, B. Rogelj, J. D. Stephenson, C. C. Miller, and D. M. McLoughlin. 2009. X11beta rescues memory and long-term potentiation deficits in Alzheimer's disease APPswe Tg2576 mice. *Hum Mol Genet* 18:4492-4500; Kotilinek, L. A., M. A. Westerman, Q. Wang, K. Panizzon, G. P. Lim, A. Simonyi, S. Lesne, A. Falinska, L. H. Younkin, S. G. Younkin, M. Rowan, J. Cleary, R. A. Wallis, G. Y. Sun, G. Cole, S. Frautschy, R. Anwyl, and K. H. Ashe. 2008. Cyclooxygenase-2 inhibition improves amyloid-betamediated suppression of memory and synaptic plasticity. *Brain* 131:651-664; Jacobsen, J. S., C. C. Wu, J. M. Redwine, T. A. Comery, R. Arias, M. Bowlby, R. Martone, J. H. Morrison, M. N. Pangalos, P. H. Reinhart, and F. E. Bloom. 2006. Early-onset behavioral and synaptic deficits in a mouse model of Alzheimer's disease. *Proc Natl Acad Sci USA* 103:5161-5166). Acute hippocampal slices from 8 month-old Tg2576 mice were perfused with 5 nM recombinant Reelin fragment complement. The inventors find that the Reelin application rescues the LTP defect in aged Tg2576 mice (FIG. 5C) suggesting that the biochemical and structural machinery involved in Reelin signaling downstream of Reelin protein processing is intact in these mice. Furthermore, it is important to note that normal levels of synaptic plasticity are obtainable in this mouse model. Reelin fragments are also associated with dense core plaques in aged (15 month-old) Tg2576 mice (FIG. 5D-G). As shown in FIG. 6, reelin and related lipoprotein receptor agonists can rescue deficits in synaptic plasticity and cognitive function that result from Aβ accumulation and/or plaque pathology. Reelin rescued the LTP deficit in 12 month-old mice modeled for AD (Tg2576) (FIG. 6).

These data are supported by Reelin associated with Aβ-containing plaques detected in the hippocampus of aged wild-type mice (Madhusudan, A., C. Sidler, and I. Knuesel. 2009. Accumulation of reelin-positive plaques is accompanied by a decline in basal forebrain projection neurons during normal aging. *Eur J Neurosci* 30:1064-1076; Knuesel, I., M. Nyffeler, C. Mormede, M. Muhia, U. Meyer, S. Pietropaolo, B. K. Yee, C. R. Pryce, F. M. LaFerla, A. Marighetto, and J. Feldon. 2009. Age-related accumulation of Reelin in amyloidlike deposits. *Neurobiol Aging* 30:697-716). In light of the established role for Reelin in synaptic function, changes in the integrity of Reelin metabolism and signaling plays a profound role in the learning and memory changes previously established in AD mouse models.

Other ligands of lipoprotein receptors have an effect on synaptic function.

Figure 7:
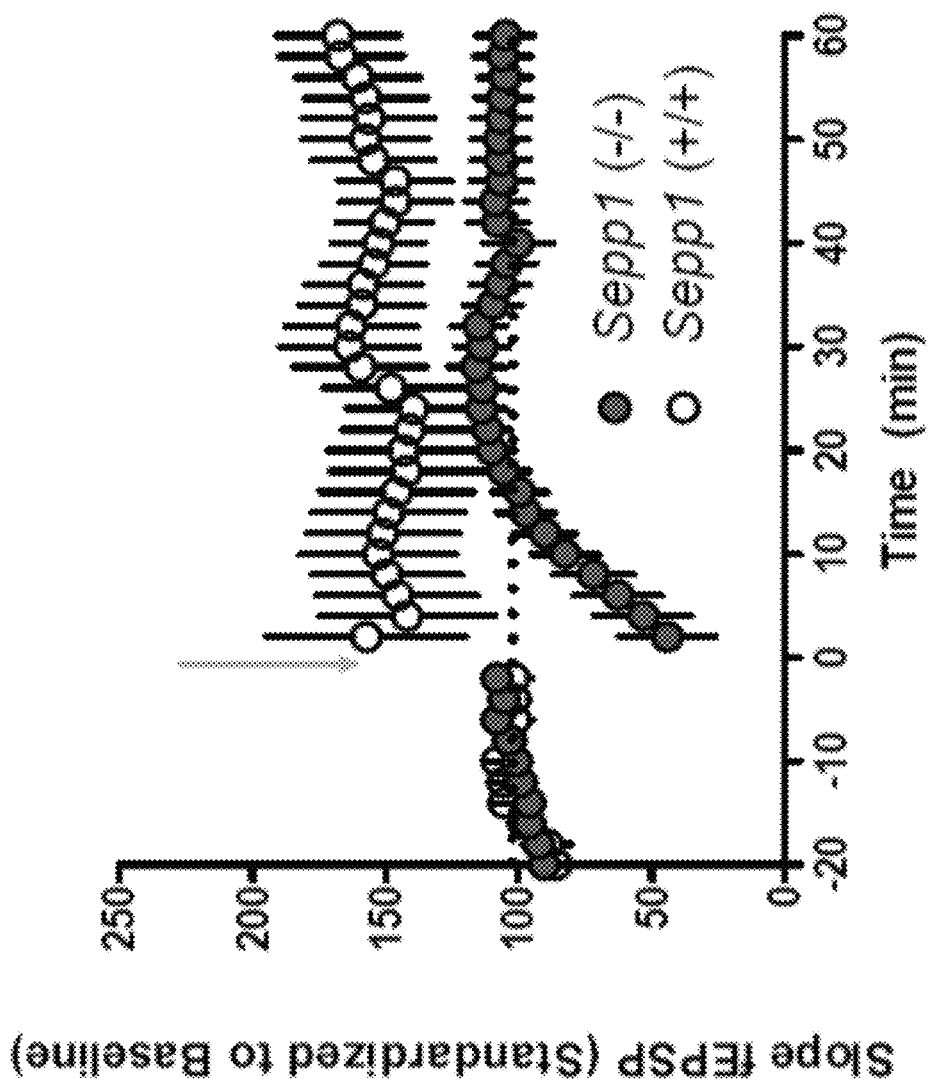
FIG. 7. Targeted deletion of the Selenoprotein P gene results in LTP deficit. Field recordings of acute hippocampal slices show no LTP after 100 Hz stimulation is given (blue arrow) SeP (−/−) n=12, SeP (+/+) n=8. Peters et at 2006

Selenium containing Selenoprotein P (SeP) has been identified as another ligand for the lipoprotein receptor ApoER2. SEP has been shown to associate with ApoER2 in the testis and in the CNS. SeP KO mice showed various pathologies, including deficits in hippocampal-dependent LTP and cognitive function (FIG. 7).

Figure 8:
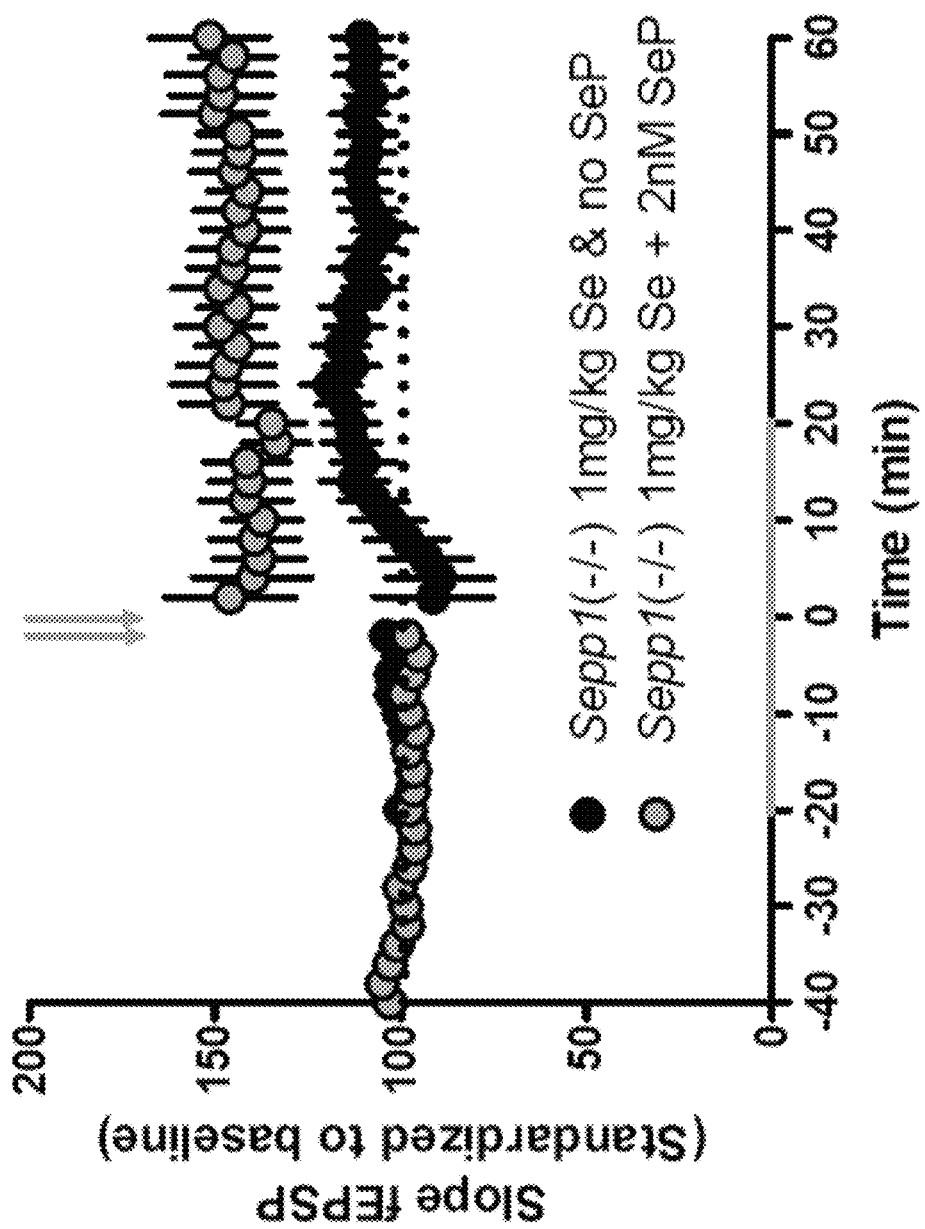
FIG. 8. Addition of Selenoprotein P rescues the LTP deficit in mice lacking the Selenoprotein P gene. Field recordings of acute hippocampal slices in SeP (−/−). Slices treated with 2 nM SeP for 20 min (red line) then given 100 Hz stimulation. SeP (−/−)+2 nM SeP n=16, SeP (−/−) no SeP n=28.

Interestingly, the LTP defect in SeP (−/−) mice can be rescued with purified SeP protein supplementation (FIG. 8). Taken together, these data suggest that SeP has a similar role to Reelin by signaling through ApoER2. It is unclear whether SeP can promote receptor clustering or compete with Reelin. However, it appears that SeP is using the ApoER2 as a receptor to internalize the SeP and deliver selenium to the neuron.

Figure 9:
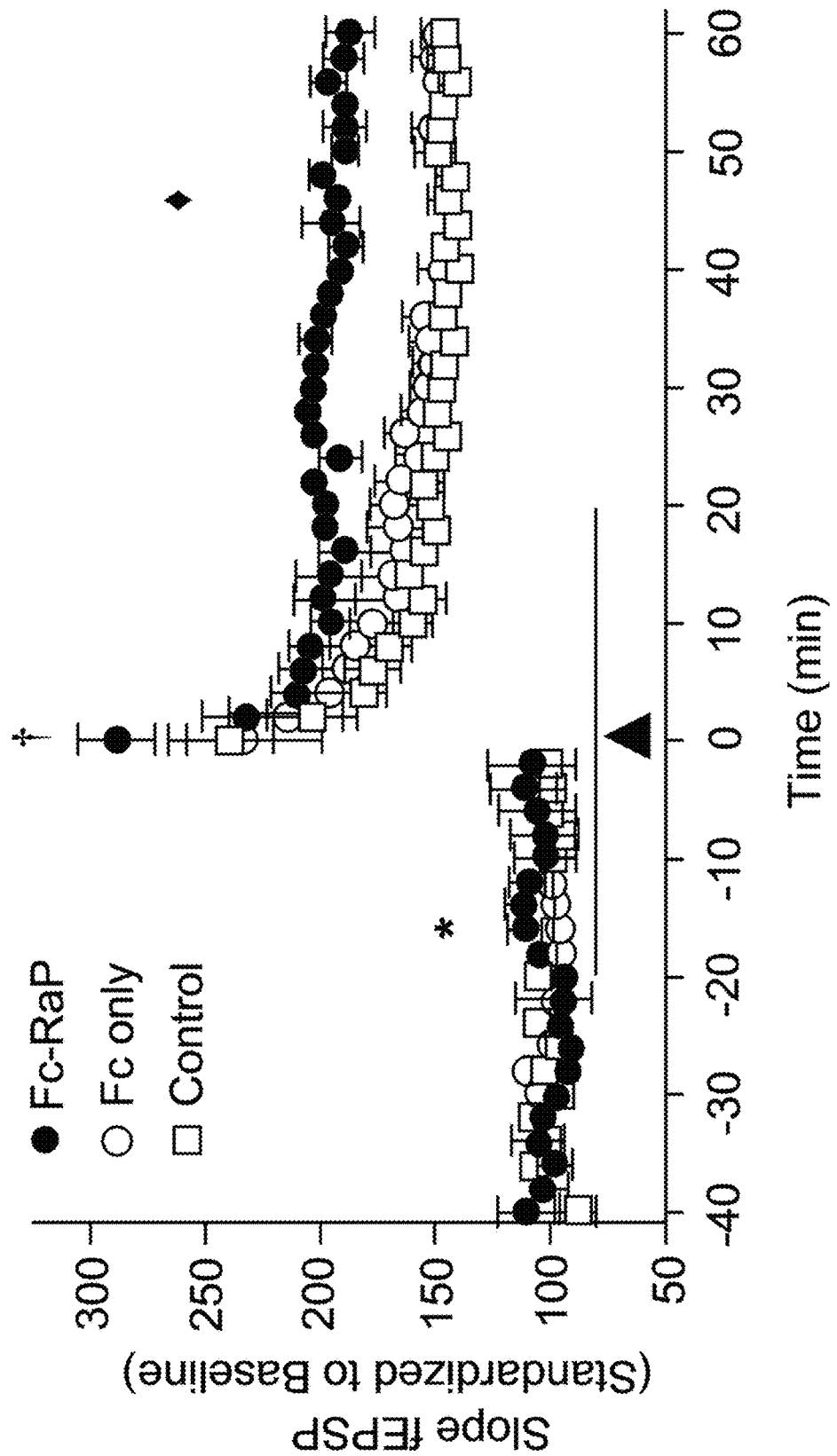
FIG. 9. Perfusion with Fc-RAP enhances hippocampal LTP induction. Hippocampal slices were perfused with Fc-RAP (10 μg/ml), Fc (10 μg/ml), or control medium. Baseline synaptic responses (marked by *) and potentiation immediately following HFS (marked by †) and up to 60 min after HFS (marked by ♦) were recorded. The arrowhead represents LTP induced with two trains of 1-s-long, 100-Hz stimulation, separated by 20 s. The horizontal line indicates application of Fc-RAP, Fc, or control medium. Results are shown as means±standard errors of the mean. fEPSP, field excitatory postsynaptic potential Strasser et al 2004.

Receptor Associated Protein (RAP) is an intracellular protein that can bind with very high affinity to the family of lipoprotein receptors. The Fc-RAP fusion protein is an engineered protein consisting of two RAP molecules connected to form a rough 'dumb bell' shape using the Fc region of an antibody. Instead of binding to and inhibiting ApoER2 and VLDLR, the Fc-RAP can cause receptor clustering and ApoER2 activation. The addition of Fc-RAP has the identical effect as reelin application by increasing LTP induction (FIG. 9). The main difference is that the Fc-RAP is likely to bind all lipoprotein receptors, but only clusters ApoER2 and VLDLR.

Reelin fragment complement in the hippocampus is altered following in vivo memory formation and ex-vivo stimulation.

Reelin is cleaved at specific sites resulting in a stable pattern of Reelin fragments easily quantified by Western blot analysis. These fragments represent potential signaling molecules with properties unique from full-length Reelin. Recombinant Reelin purified from stably transfected HEK293 cells contains fragments of the same size as the major fragments found in the hippocampus. Application of recombinant Reelin fragment compliment can (1) increase synaptic transmission by facilitating AMPA receptor insertion and increasing NMDA receptor function, (2) reduce silent synapses, (3) modify synaptic morphology and (4) enhance LTP (Qiu, S., and E. J. Weeber. 2007. Reelin signaling facilitates maturation of CA1 glutamatergic synapses. *J Neurophysiol* 97:2312-2321; Qiu, S., K. M. Korwek, A. R. Pratt-Davis, M. Peters, M. Y. Bergman, and E. J. Weeber. 2006. Cognitive disruption and altered hippocampus synaptic function in Reelin haploinsufficient mice. *Neurobiol Learn Mem* 85:228-242).

Additionally, fear conditioned learning produces changes in the endogenous Reelin fragment complement. The inventors found a dramatic change in Reelin expression and fragment complement over the 18 hours following contextual fear conditioning, particularly in the 450 and 180 kDa fragments (FIG. 10).

Figure 10A:
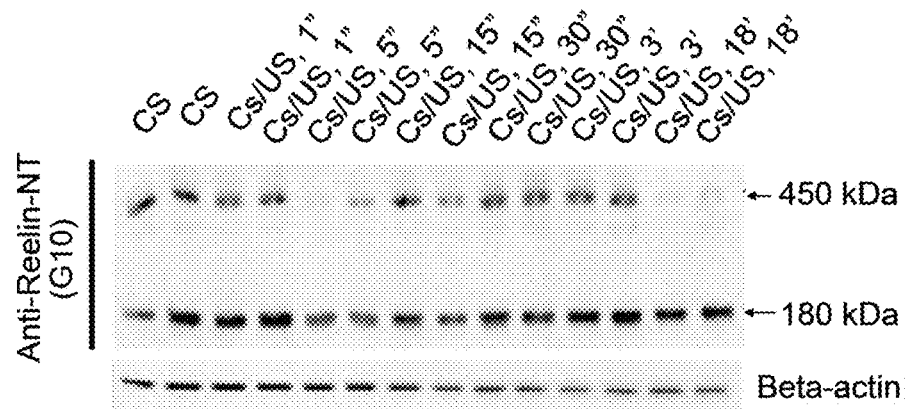
FIG. 10A. Contextual fear conditioning alters Reelin levels. Wild type mice were trained with a 3-shock, contextual fear conditioning protocol (CFC). Non-shocked mice (CS) were used as a negative control and shocked, context-exposed mice (CS/US) had their hippocampus removed at 1, 5, 15, 30, and 180 minutes after training, as well as 18 hours post-training (n=4, time point). Reelin was detected in hippocampal homogenates using anti-Reelin (G10).
Figure 10B:
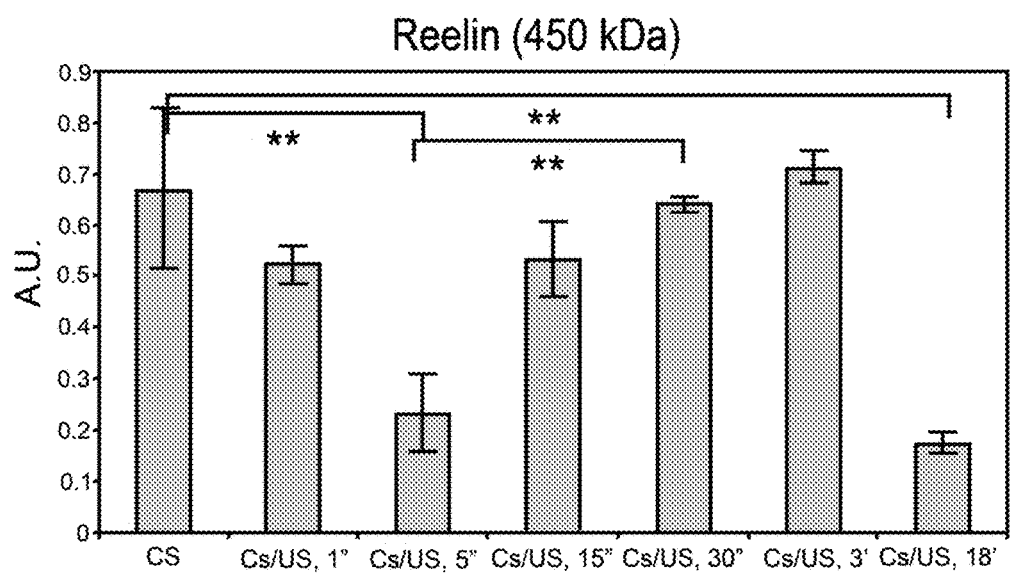
FIG. 10B. Contextual fear conditioning alters Reelin levels. Wild type mice were trained with a 3-shock, contextual fear conditioning protocol (CFC). Non-shocked mice (CS) were used as a negative control and shocked, context-exposed mice (CS/US) had their hippocampus removed at 1, 5, 15, 30, and 180 minutes after training, as well as 18 hours post-training (n=4, time point). Reelin was detected in hippocampal homogenates using anti-Reelin (G10) and the levels of full-length Reelin were quantitated. The asterisks denote statistical significance following a two-tailed t-test, where $p<0.5$.
Figure 11A:
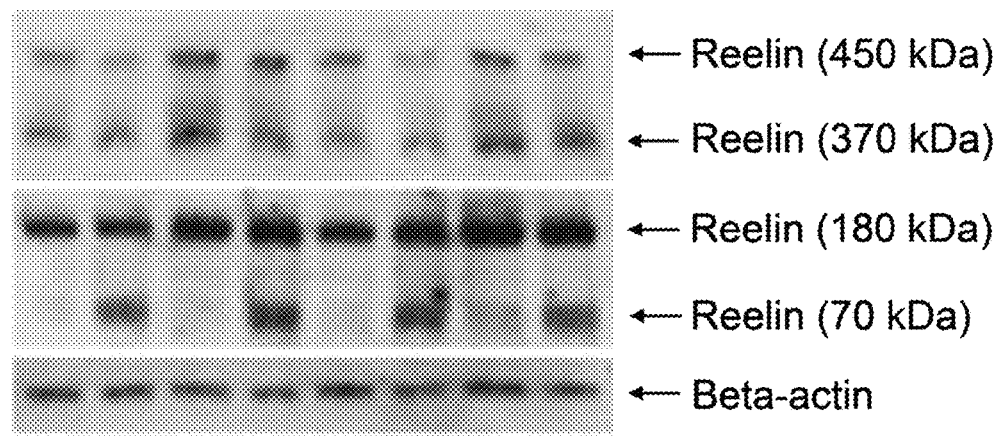
FIG. 11A. HFS alters Reelin metabolism in a tPA-dependent manner. Acute hippocampal slices were stimulated using TB-STIM (theta burst stimulation) consisting of 5 trains at theta-burst across the Schaffer collateral. Hippocampi were harvested 15 minutes later and homogenates were subjected to western blot analysis and detected with anti-Reelin (G10) (n=3 per group). Non-stimulated is denoted as NS and stimulated as S.
Figure 11B:
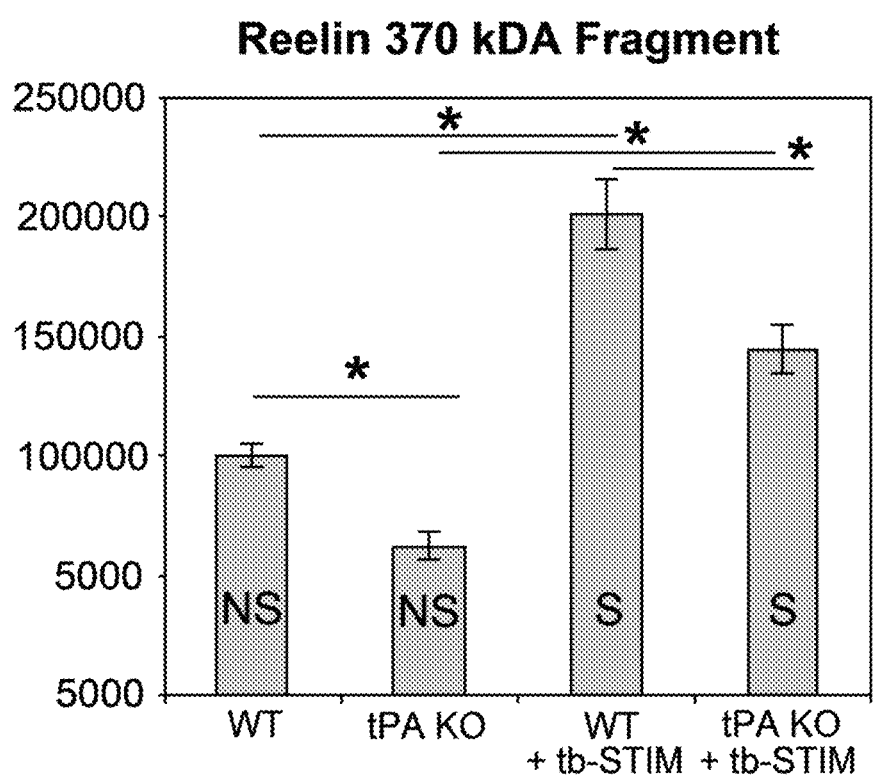
FIG. 11B. HFS alters Reelin metabolism in a tPA-dependent manner. A graph showing quantified results of acute hippocampal slices stimulated using TB-STIM (theta burst stimulation) consisting of 5 trains at theta-burst across the Schaffer collateral. Hippocampi were harvested 15 minutes later and homogenates were subjected to western blot analysis and detected with anti-Reelin (G10) (n=3 per group). Non-stimulated is denoted as NS and stimulated as S. The 370 kDa was quantified and statistically analyzed using a two tailed t-test (*, $p<0.05$).
Figure 12A:
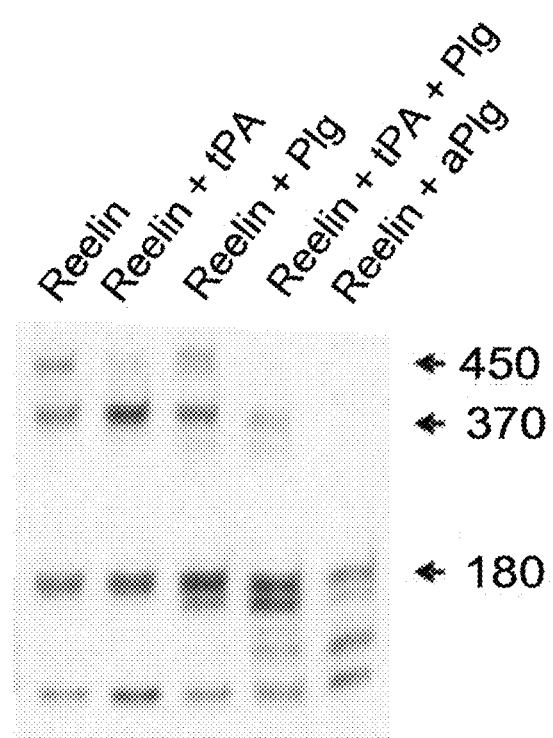
FIG. 12A. tPA modulates Reelin processing. The ability of tPA/plasminogen to affect Reelin processing was determined by reacting Reelin (50 nM) with tPA (60 ug/ml), inactive plasminogen (18 ug/ml), tPA and plasminogen, and Plasmin (active, 0.5 U/ml) in PBS for 45 minutes at 37° C. Reactions were run on Westerns (at 1:10) and probe with anti-Reelin (G10, an N-R2 recognizing antibody) and ant-I Reelin (Ab14, a R7-8 recognizing antibody).
Figure 12B:
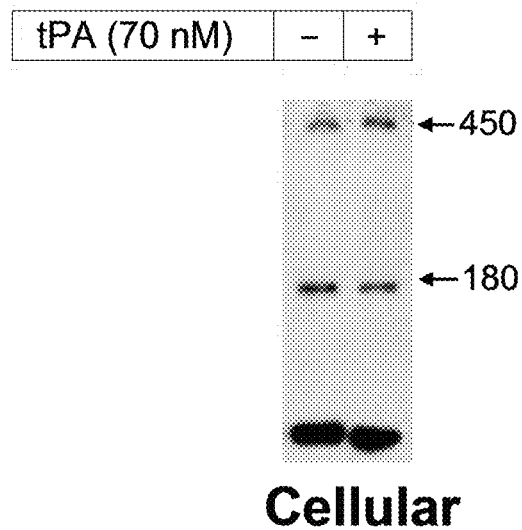
FIG. 12B. tPA modulates Reelin processing. The ability of tPA to affect Reelin metabolism in primary cortical neurons was determined by incubating cells in fresh supernatant for 24 hours with 70 nM tPA for cellular extracts subjected to Western analysis and detection with G10.
Figure 12C:
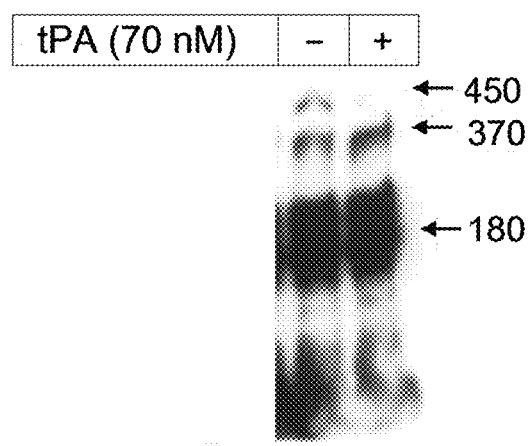
FIG. 12C. tPA modulates Reelin processing. The ability of tPA to affect Reelin metabolism in primary cortical neurons was determined by incubating cells in fresh supernatant for 24 hours with 70 nM tPA for supernatant protein extracts subjected to Western analysis and detection with G10.
Figure 12D:
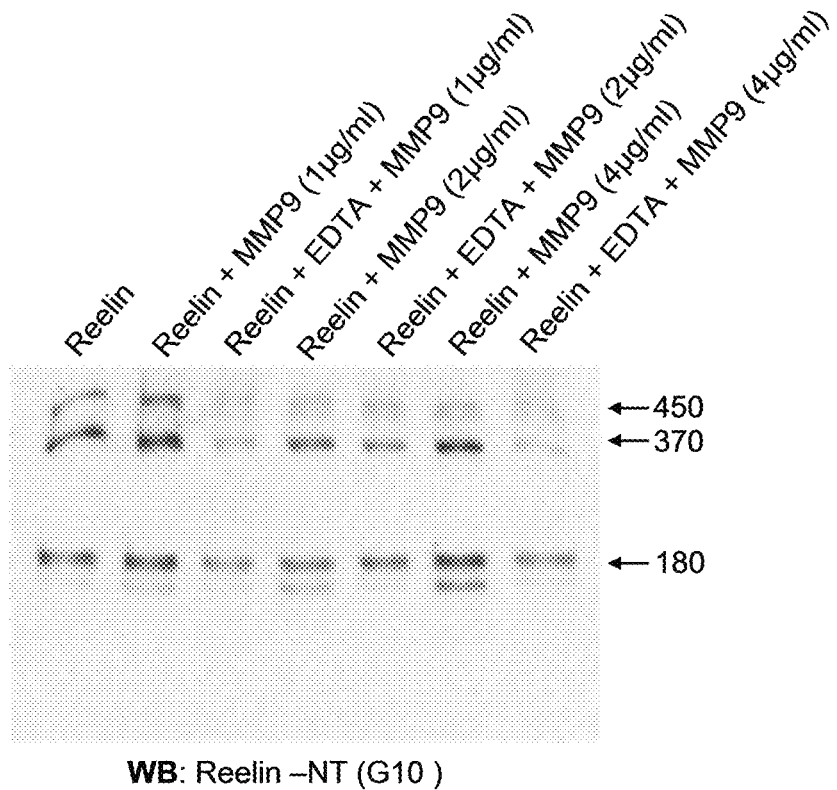
FIG. 12D. MMP-9 modulates Reelin processing. The ability of MMP-9 (active; Calbiochem, PF140) to affect Reelin processing was determined by reacting Reelin (50 nM) with different concentrations of MMP-9 (1-4 ug/ml) in PBS at 37° C. for 3 hours. EDTA (10 mM) was included as a negative control, as it blocks MMP9 activity. Western blots were run on 1:10 of the reaction and probed with anti-Reelin (G10). The ability of MMP-9 (250 nM) and the MMP-9 inhibitor (25 nM; Calbiochem 444278) to affect Reelin processing in primary cortical neurons was determined after 24 hours in both cellular and supernatant extracted proteins.
Figure 12E:
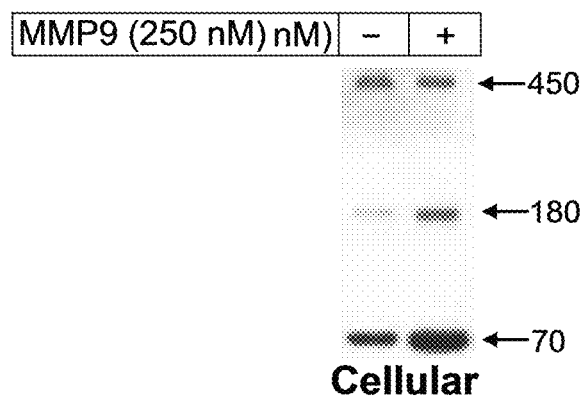
FIG. 12E. MMP-9 modulates Reelin processing. The ability of MMP-9 (active; Calbiochem, PF140) to affect Reelin processing was determined using the cellular fraction by reacting Reelin (50 nM) with different concentrations of MMP-9 (1-4 ug/ml) in PBS at 37° C. for 3 hours. Western blots were run on 1:10 of the reaction and probed with anti-Reelin (G10). The ability of MMP-9 (250 nM) and the MMP-9 inhibitor (25 nM; Calbiochem 444278) to affect Reelin processing in primary cortical neurons was determined after 24 hours in the cellular fraction.
Figure 12F:
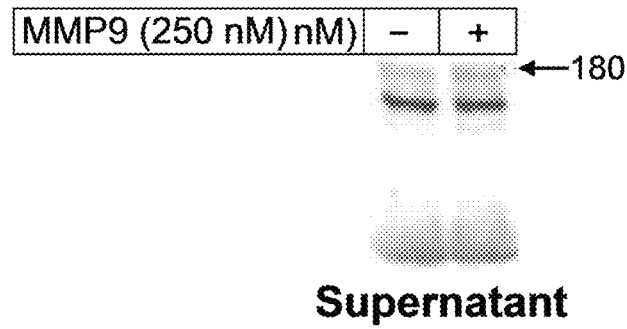
FIG. 12F. MMP-9 modulates Reelin processing. The ability of MMP-9 (active; Calbiochem, PF140) to affect Reelin processing was determined using the supernatant protein fraction by reacting Reelin (50 nM) with different concentrations of MMP-9 (1-4 ug/ml) in PBS at 37° C. for 3 hours. Western blots were run on 1:10 of the reaction and probed with anti-Reelin (G10). The ability of MMP-9 (250 nM) and the MMP-9 inhibitor (25 nM; Calbiochem 444278) to affect Reelin processing in primary cortical neurons was determined after 24 hours in the supernatant extracted proteins.
Figure 12G:
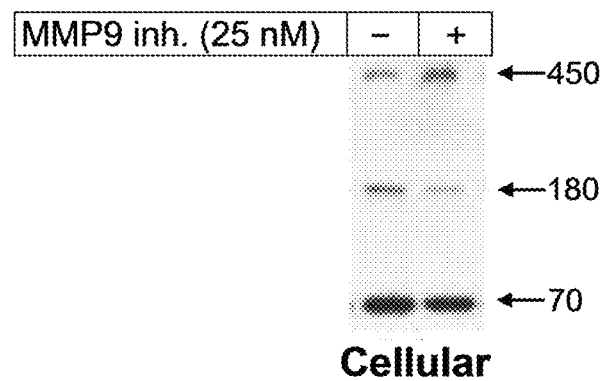
FIG. 12G. MMP-9 modulates Reelin processing. The ability of MMP-9 (active; Calbiochem, PF140) to affect Reelin processing was determined using the cellular fraction by reacting Reelin (50 nM) with different concentrations of MMP-9 (1-4 ug/ml) in PBS at 37° C. for 3 hours along with EDTA (10 mM) as a negative control, as it blocks MMP9 activity. Western blots were run on 1:10 of the reaction and probed with anti-Reelin (G10). The ability of MMP-9 (250 nM) and the MMP-9 inhibitor (25 nM; Calbiochem 444278) to affect Reelin processing in primary cortical neurons was determined after 24 hours in the cellular fraction.
Figure 12H:
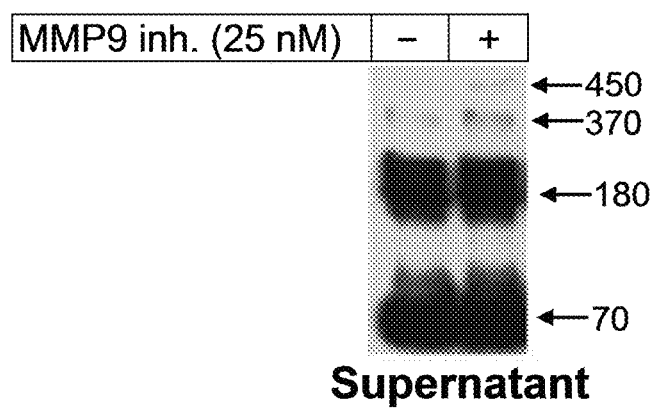
FIG. 12H. MMP-9 modulates Reelin processing. The ability of MMP-9 (active; Calbiochem, PF140) to affect Reelin processing was determined using the supernatant protein fraction by reacting Reelin (50 nM) with different concentrations of MMP-9 (1-4 ug/ml) in PBS at 37° C. for 3 hours along with EDTA (10 mM) as a negative control, as it blocks MMP9 activity. Western blots were run on 1:10 of the reaction and probed with anti-Reelin (G10). The ability of MMP-9 (250 nM) and the MMP-9 inhibitor (25 nM; Calbiochem 444278) to affect Reelin processing in primary cortical neurons was determined after 24 hours in the supernatant extracted proteins.

Moreover, theta burst stimulation delivered to the Schaffer collateral pathway led to significant increases in Reelin expression and fragment cleavage at 15 minutes post-stimulation (FIG. 10). These results show that integration and control of Reelin signaling responsible for alterations in synaptic plasticity and modulation of learning and memory involves the processing of Reelin into functionally-distinct fragments.

The inventors also found that the efficacy of generating the 370 kDa product to be partially dependent on a candidate Reelin-cleaving enzyme, tPA. This potential mechanism of regulation has profound implications on how this signaling system is integrated into known mechanisms of neuronal regulation and coordinated to participate in physiological processes such as learning and memory.

MMP-9- and tPA-Mediated Reelin Processing.

Recently it was shown that the processing of Reelin by metalloproteinase(s) is essential for normal cortical plate formation (Jossin, Y., and A. M. Goffinet. 2007. Reelin signals through phosphatidylinositol 3-kinase and Akt to control cortical development and through mTor to regulate dendritic growth. *Mol Cell Biol* 27:7113-7124), though the specific enzyme responsible remains as yet unknown. This discovery suggests that metalloproteinase-mediated Reelin processing may be important for directed Reelin signaling in the adult brain as well. Both tPA and MMP-9 are candidate metalloproteinases with clearly demonstrated roles in regulating synaptic plasticity and cognitive function (Bozdagi, O., V. Nagy, K. T. Kwei, and G. W. Huntley. 2007. In vivo roles for matrix metalloproteinase-9 in mature hippocampal synaptic physiology and plasticity. *J Neurophysiol* 98:334-344; Nagy, V., O. Bozdagi, A. Matynia, M. Balcerzyk, P. Okulski, J. Dzwonek, R. R. Costa, A. J. Silva, L. Kaczmarek, and G. W. Huntley. 2006. Matrix metalloproteinase-9 is required for hippocampal late-phase long-term potentiation and memory. *J Neurosci* 26:1923-1934; Huang, Y. Y., M. E. Bach, H. P. Lipp, M. Zhuo, D. P. Wolfer, R. D. Hawkins, L. Schoonjans, E. R. Kandel, J. M. Godfraind, R. Mulligan, D. Collen, and P. Carmeliet. 1996. Mice lacking the gene encoding tissue-type plasminogen activator show a selective interference with late-phase longterm potentiation in both Schaffer collateral and mossy fiber pathways. *Proc Natl Acad Sci USA* 93:8699-8704; Pang, P. T., and B. Lu. 2004. Regulation of late-phase LTP and long-term memory in normal and aging hippocampus: role of secreted proteins tPA and BDNF. *Ageing Res Rev* 3:407-430; Zhuo, M., D. M. Holtzman, Y. Li, H. Osaka, J. DeMaro, M. Jacquin, and G. Bu. 2000. Role of tissue plasminogen activator receptor LRP in hippocampal long-term potentiation. *J Neurosci* 20:542-549; Baranes, D., D. Lederfein, Y. Y. Huang, M. Chen, C. H. Bailey, and E. R. Kandel. 1998. Tissue plasminogen activator contributes to the late phase of LTP and to synaptic growth in the hippocampal mossy fiber pathway. *Neuron* 21:813-825).

Figure 13A:
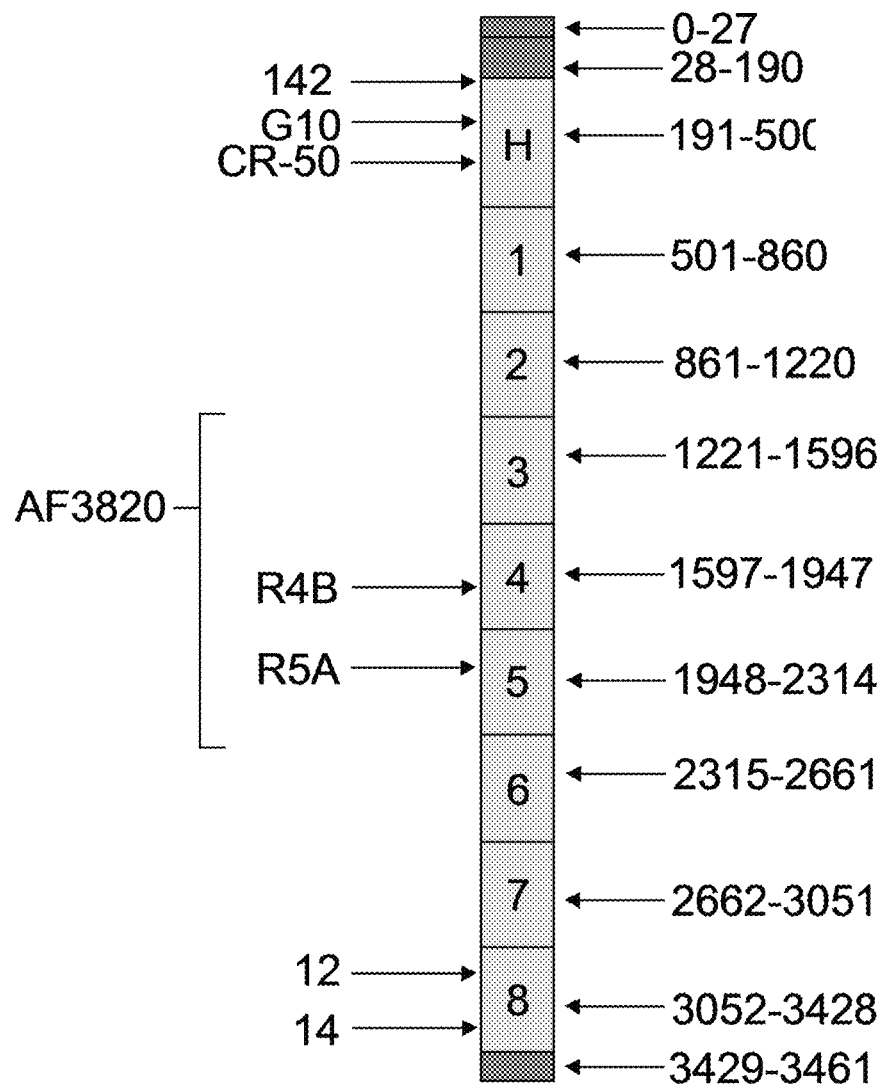
FIG. 13A. Tri-epitope mapping. Reelin consists of an N-terminal region followed by the CR-50 electrostatic domain (purple), an F-spondin domain (H), and 8 consecutive EGF-like repeats.
Figure 13B:
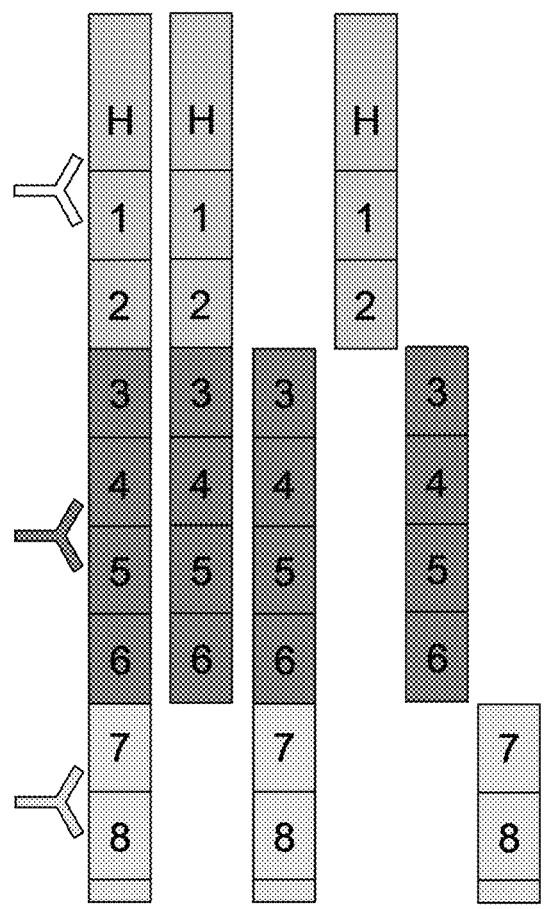
FIG. 13B. Tri-epitope mapping. Antibodies that distinctly recognize the N-R2, R3-R6, and R7-R8 regions of Reelin can be used to determine the distribution of full-length Reelin and its major fragments.

Reelin is processed by both tPA and MMP-9 to generate the major Reelin fragment products found in vivo (FIG. 12A-C, 12D-H). As it can be seen, tPA increases the 370 kDa (N-R6) and 80 kDa (R7-8) fragments under cell free conditions (FIG. 12A-C), indicating that tPA cleaves Reelin between R6-R7 (FIG. 13). Cleavage of Reelin by Plasmin results in a spectrum of products of previously unknown identity and specific retention of the 180 kDa fragment. Application of recombinant tPA to primary neurons resulted in a complete conversion of extracellular Reelin from full-length to the 370 and 180 kDa forms, and a decrease in intracellular 180 kDa Reelin. Furthermore, MMP-9 increases both the 370 kDa (N-R6) and 180 kDa (N-R2) fragments, as well as a fragment found just below the well known 180 kDa fragment (FIG. 12D-H). These results under cell free conditions support that MMP-9 can cleave Reelin at both cleavage sites, R2-3 and R6-7; however, application of MMP-9 to primary neurons led to a specific accumulation of the 180 kDa fragment in cells and MMP-9 inhibition for 24 hours led to a dramatic increase in full-length cellular Reelin and decrease in cellular 180 kDa Reelin. These results suggest that under normal conditions, MMP-9 is responsible for cleaving Reelin between R2-R3 (See fragment map; FIG. 13). Taken together, these preliminary data suggest that MMP-9 and tPA are sufficient for generation of the major Reelin fragments found in vivo.

As shown above, reelin protein processing in the hippocampus is susceptible to in vitro and in vivo synaptic activity. It also appears that MMP-9 and tPA are involved in the process of Reelin metabolism. Surprisingly, a single exogenous Reelin application enhances learning and memory for at least eleven days in adult wild-type mice. When considering the role of lipoprotein receptors in Aβ clearance, and the identification of Reelin association to Aβ plaques in an AD mouse model, the question of the role of Reelin in the etiology and pathogenesis of AD becomes a timely and important area of research. Moreover, the now improved understanding of the mechanisms and implications of Reelin processing provides, inter alia, AD therapeutic interventions aimed toward removal of Aβ and improvement of cognitive function.

Moreover, all that is known regarding Reelin localization in the adult brain has been generated using an antibody that recognizes the N-R2 region. The N-R2 region is present in the full-length (N-R8), N-R2 and N-R6 fragments of Reelin, but not in the other major fragments. Therefore, the 3-epitope mapping approach ((FIG. 13) affords unprecedented spatial resolution to monitor changes in Reelin product production and localization.

Figure 14:
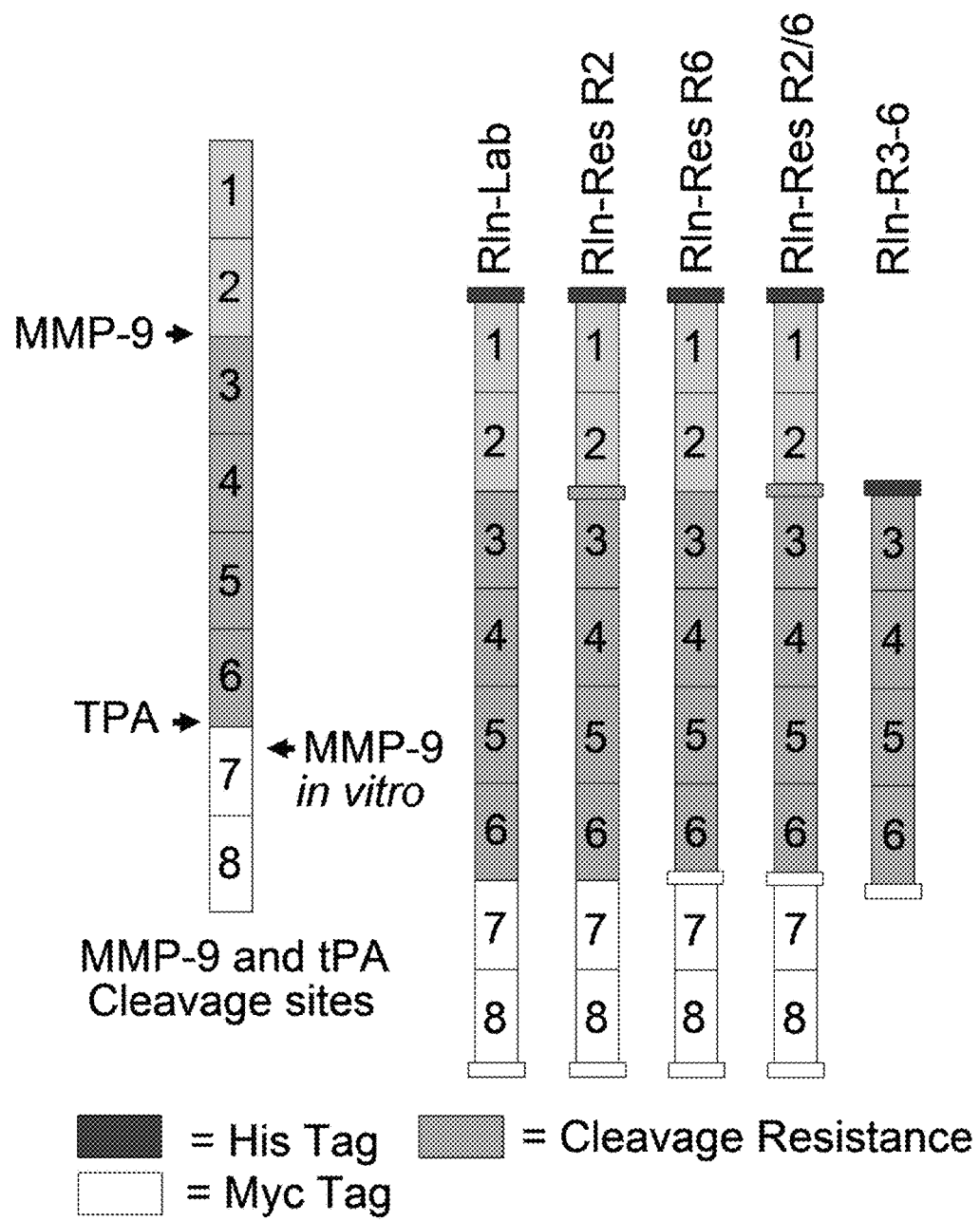
FIG. 14. Illustration of constructs to be used in SA2 and SA3 and sites of Reelin cleavage. MMP-9 can cleave between regions 2 and 3, but has also been shown to cleave in region 7 during in vitro reactions only. tPA can cleave between regions 6 and 7. Proposed constructs are made without the in vitro MMP-9 binding site a with both C and N terminal tags. Rln-Res=Reelin Cleavage Resistant; Rln-Lab=Reelin labile.

In order to characterize specific fragments produced by tPA- and MMP-9-dependent Reelin processing in the context of normal synaptic function and memory formation, the inventors generated cleavage-resistant Reelin mutant constructs using site-directed mutagenesis FIG. 14). Reelin mutants include constructs resistant to cleavage (Rln-Res) by tPA at R2-3, to MMP-9 at R6-7 and to both enzymes at R2-3 and R6-7. Fragments mimicking cleavage by tPA or MMP-9 with, or without a cleavage resistant site are also contemplated. One complementary Reelin construct is tagged in an identical fashion as the Rln-Res protein; however, it does not contain the two altered sites for cleavage (Reelin cleavage labile; FIG. 14)). A tagged fragment produced with both sites mutated (negative control construct) and a tagged R3-6 fragment shown to bind ApoER2 and VLDLR (potential positive control) is included. The Reelin constructs are sub-cloned into mammalian expression vectors containing N-terminal polyhistidine tags and/or C-terminal Myc tags to allow later recognition of exogenous Reelin. The exact cleavage sites can be identified by using purified full-length Reelin reacted with either tPA or MMP-9 therefore the resultant fragments can be isolated.

Reelin Application Recovers Spine Density in HRM and Reelin-Null Mice

In cultured hippocampal neurons, reelin signaling is required for normal development of dendritic structures. In the absence of reelin or the intracellular adaptor protein Dab1, neurons exhibit stunted dendritic growth and a reduction in dendritic branches, a phenotype analogous to that seen in neurons lacking the reelin receptors apoER2 and VLDLR (Niu S, Renfro A, Quattrocchi C C, Sheldon M, D'Arcangelo G. Reelin promotes hippocampal dendrite development through the VLDLR/ApoER2-Dab1 pathway. Neuron 2004; 41:71-84). The HRM exhibits a deficit in hippocampal-dependent contextual fear conditioned learning and synaptic plasticity in area CA1 of the hippocampus. It is believed that these behavioral and physiologic phenotypes of the HRM are due in part to reduced or inhibited synaptic connectivity. This is supported by the observation that HRM have a reduction in spine density (FIG. 15).

Dendritic spines are small protrusions that cover the surface of dendrites and bear the postsynaptic structures that form excitatory synapses. Abnormal shapes or reduced numbers of dendritic spines are found in a number of cognitive diseases, such as Fragile X syndrome, William's syndrome, Rett syndrome, Down's syndrome, Angelman syndrome and autism. A reduction in the number of dendritic spines suggests that a constitutive level of reelin/lipoprotein receptor-mediated signaling is required for development of dendritic structures, which are crucial for intensive information processing by the neurons. This notion is in agreement with studies showing that heterozygote reeler mice exhibit reduced dendritic spine densities and impaired performance in certain learning and memory behaviors.

Hippocampal neurons cultured from reeler embryos had significantly less dendritic spines, a phenotype that can be rescued by addition of exogenous recombinant reelin to the culture. Organotypic hippocampus cultures were created from 6-7 day-old wild-type, HRM and Reelin-deficient mice and treated with 5 nm Reelin for 21 days. Fluorescent dye was injected into neuronal cells by administering whole cell patch clamp current and the cells were visualized under the confocal microscope after fixation. Reelin-treated of HRM cells showed an increase in dendritic spine density after 21 days compared to age matched neurons from wild-type culture (FIG. 15B). In contrast, mock (conditioned media from non-stably transfected cells) application showed no change in spine density (FIG. 15C). The same experiment in reelin knockout mice showed that reelin application also rescued the dendritic spine density compared to mock controls (FIGS. 15C and 15F). Both the reelin treated cells resembled the dendritic spine morphology seen in WT cells (FIG. 15D) and when quantified, dendritic spines significantly increased in reelin-treated HRM cultures compared to mock treated controls and are similar to spine density levels observed in wild-type cultures (FIG. 15A).

Treatment of organotypic cultures consisted of repeated 5 nM Reelin application every 3 days for 21 days. To verify that this application protocol represented a chronic application of reelin, and reelin was not being degraded or actively removed from the media, the inventors removed 15 ul of media from culture plates at times of 0, 6, 12, 24, 48, 72, and 96 hours following reelin application. Western analysis of these aliquots showed no degradation or reduction in Reelin (FIG. 15G). Thus, the increase in spine density is due to reelin present at physiologic relevant levels for the entire 21 day application.

In Vivo Reelin Application Effects on Overall Behavioral Responses.

Mice lacking reelin exhibit abnormal lamination of neuronal layers, which is most severely seen in the cortex, cerebellum, and hippocampus. The Reelin knockout exhibits the "reeler" phenotype, characterized by rest tremor and ataxia. Although the Cajal-Retzius cells eventually degenerate after the completion of development, reelin continues to be expressed by GABAergic interneurons in the cortex and hippocampus. In the adult, as in the developing brain, Reelin's molecular effects are mediated through two receptors: the very low density lipoprotein receptor (VLDLR) and the apolipoprotein E receptor 2 (ApoER2). Reelin-dependent signaling through ApoER2 and VLDLR occurs through hetero- or homo-dimerization of receptors and can activate the CDK-5 and PI3-K signal transduction pathways. Reelin signaling is also linked to modulation of synaptic plasticity and memory formation.

The heterozygote reelin mouse (HRM) exhibits haploinsufficiency and a 50% reduction in reelin protein levels, but does not lead to an overt "reeler" phenotype. Instead, Reelin haploinsufficiency manifests as very subtle neuroanatomical, physiologic and behavioral deficits. These include a decrease in dendritic spines in the parietal-frontal cortex (PFC) pyramidal neurons in addition to basal dendritic cells of hippocampal CA1 pyramidal neurons and cortical neuropil hypoplasia. The HRM displays a reduced density of nicotinamide-adenine dinucleotide phosphate-diaphorase (NADPH-d)-positive neurons in the cortical gray matter, altered dopaminergic markers in the mesotelencephalic dopamine pathway. The HRM shows impaired short-term and long-term plasticity in hippocampal CA1 synapses. Long-term potentiation (LTP) is disrupted using both high frequency stimulation and pairing stimulation protocols. Behaviorally, the HRM exhibits an age-dependent decrease in prepulse inhibition.

The HRM has often been referred to as a possible mouse model for human schizophrenia. Reelin mRNA and protein levels are reduced in post-mortem brains of schizophrenic patients resulting in approximately 50% of that found in normal control post mortem brains. Investigation of the Reeler heterozygote found other similarities to the human condition, including: decreased GAD67 expression, decreased tactile and acoustic prepulse inhibition, and reduced spine density. Schizophrenia is also associated with severe cognitive impairment and disordered thinking. This manifests as a lack of overall attention, impairment of information processing disrupting both declarative and non-declarative memories. Importantly, HRM show a similar cognitive dysfunction, observed as reduced associative fear conditioned learning.

An HRM breeding pair (B6C3Fe a/a-Reln$^{rl}$/+ strain) was obtained from the Jackson Laboratory. The offspring of both HRM were genotyped by using genomic DNA from a 2 mm diameter earpunch. The primer sequences were, forward: 5'-taatctgtcctcactctgcc-3' (SEQ ID NO:1); reverse: 5'-acagt-tgacataccttaatc-3' (SEQ ID NO:2); reverse mutated: 5'-tg-cattaatgtgcagtgttgtc-3'(SEQ ID NO:3). Animal care and use protocol was approved by the Institutional Animal Care and Use Committee of Vanderbilt University.

The culmination of research on Reelin's actions in developing CNS and adult cognitive processes raises the question of whether the cognitive deficits in HRM are due to reelin haploinsufficiency, leading to a decrease in signal transduction and LTP formation, or reduction in dendritic spines, resulting in decreased information processing and storage in areas involved in learning and memory. Alternatively, HRM show reduced spine density, thus, these deficits may be due to developmental defects that result in the mis-wiring of critical regions of the CNS.

The increase in sEPSCs in wild-type mice, but not in Reelin knockout mice despite chronic reelin exposure indicated that spine formation was not the sole factor influencing spontaneous synaptic activity in cultured neurons. This would suggest that developmental abnormalities resulting in altered synaptic connectivity in the hippocampus of HRM, and to a greater extent in the Reelin-deficient mice, were the underlying basis for the cognitive deficits in the HRM.

The HRM and wild-type mice are similar for open field and elevated plus maze. These behavioral tests are essential for evaluation and proper determination of associative fear conditioning results. In addition, the open field and elevated plus maze tasks allow assessment of any differences in locomotor activity or anxiety after the cannulation placement and injection.

For the open field tests, general locomotor activity was measured using the open field task. Animals were placed in the open field (27×27 cm) chamber for 15 min in standard room-lighting conditions. Activity in the open field was monitored by 16 photoreceptor beams on each side of the chamber and analyzed by a computer-operated (Med Associates) animal activity system.

For the elevated plus maze experiments, mice were placed in the elevated plus maze one hour after they had completed the open field task to test their levels of anxiety. The apparatus consisted of two opposing open arms (30 cm×5 cm) and two opposing closed arms (30 cm×5 cm×15 cm) connected by a central square platform and was 40 cm above the ground. Testing took place under standard-lighting conditions. Mice were placed in the open arms facing the closed arms at the beginning of the 5 minute session. The number of entries and the total time spent in the open arms were recorded.

Bilateral intracerebroventricular cannulations on HRM mice were followed by evaluating open field and elevated plus maze tests. Following a 5 day recovery period from the surgical procedure, these mice were injected with 1 ul of either mock or reelin through two PE50 tubes attached to two Hamilton syringes. Mice were visually assessed daily for overall health following surgery. All mice used for these studies showed no signs of infection assessed by visual inspection of the site of incision and rectal temperature monitored daily.

The injection of 1 ul of a concentrated Reelin solution represented a final distributed concentration of 5 nM. To test for dispersion of Reelin cannulated wild type mice were injected monolateral with 1 ul Reelin and sacrificed 1 hour following injection. Brains were fixed and immunohistochemical analysis for Reelin was performed. No discernable distribution of Reelin was seen in the Reelin injected hemisphere, however, an increase in overall Reelin immunoreactivity was observed in the treated versus non treated hemispheres. This suggests that Reelin quickly diffuses from the ventricle by the time of behavioral testing.

One hour after Reelin injection the experimental mice were placed in the open field chamber and distance traveled over a 15 minute period was measured. Immediately following the open field task, mice were placed in the elevated plus maze and the number of entries and percent time in the open arms were measured. A greater amount of time spent in the closed arms compared to the open arms is an index of higher anxiety. No differences were seen between the mock and reelin treated heterozygote mice in these two tasks (FIG. 16A-C).

Mice normally exhibit a startle response to loud noise but if a moderate noise is presented prior to the loud noise, the startle response is attenuated, an effect known as prepulse inhibition (PPI). PPI represents another compelling behavioral phenotype of the HRM that recapitulates human schizophrenia. PPI was performed one hour after elevated plus maze. The mouse was placed in a Plexiglas cylinder in a dark PPI chamber (Med Associated Inc.; St. Albans, Vt.) with the presence of background noise provided by a fan. After mice were allowed to acclimate for 5 minutes in the chamber, they were underwent a random presentation of five stimulus trial types: 120 db stimulus startle alone, and each of a 70, 76, 82, and 88 db prepulse followed by a 120 db startle for a total of 9 trials per type. The percent prepulse inhibition and the peak startle were measured using the Startle Reflex 5 software.

The inventors have previously shown that the HRM show a deficit in PPI, specifically at the 82 dB prepulse. To determine whether Reelin rescues this deficit, the inventors performed PPI in Reelin-injected cannulated mice. Following the elevated plus maze, mice were placed in the startle reflex chamber and given a random presentation of 5 trial types: no prepulse with a 120 dB acoustic startle, or 70, 76, 82, 88 dB prepulses with a 120 dB acoustic startle. The inventors saw that there was no difference in the startle to acoustic stimulation, where no prepulse was presented with a 120 dB acoustic startle between the mock treated and reelin treated HRM (FIG. 16E). Additionally, there was no difference in the PPI between both treatment groups at any of the prepulse levels (FIG. 16D).

The HRM shows a deficit in associative learning when compared to their wild-type littermates. Contextual fear conditioning was performed on Reelin and Mock-treated HRM at 5 hours post-injection to assess whether Reelin haploinsufficiency is responsible for this change rather than permanent developmental defects. Fear conditioning was performed 2 hours after PPI. The conditioning chamber (26×22×18 cm; San Diego Instruments, San Diego, Calif.) was made of Plexiglas and was equipped with a grid floor for delivery of the unconditioned stimulus (US) and photobeams to monitor activity. The conditioning chamber was placed inside a soundproof isolation cubicle.

Training occurred in the presence of white light and background noise generated by a small fan. Each mouse was placed inside the conditioning chamber for 2 minutes before the onset of a conditioned stimulus (CS), an 85 dB tone, which lasted for 30 seconds. A 2 sec US foot-shock (0.5 mA) was delivered immediately after the termination of the CS.

Each mouse remained in the chamber for an additional 60 seconds, followed by another CS-US pairing. Each mouse was returned to its home cage after another 30 seconds. The test for contextual fear memory was performed 1, 24, and 72 hours after training by measuring freezing behavior during a 3 minute test in the conditioning chamber.

Freezing was defined as lack of movement in each 2 second interval. Cued fear memory was tested in the presence of red light, vanilla odor, and the absence of background noise. The grid floor was covered and the walls were covered with alternating black and white plastic panels. Each mouse was placed into this novel context for 3 minutes at 1 hour and 24 hours after training. They were exposed to the CS for another 30 min following this. Freezing behavior was recorded and processed by the SDI Photobeam Activity System software throughout each testing session.

The aversive unconditioned stimulus (US), a 5 mA foot-shock, was paired twice with an auditory tone (conditioned stimulus, CS). During the training period, both animals showed similar levels of freezing after the presentation of the US with an increasing trend of freezing (FIG. 17A). This indicates that the acquisition of the fear memory is similar in both groups and freezing ability is similar. Mice were placed back into the context in which they were trained at 1, 24 or 72 hours following training. There was no difference between the Reelin treated mice compared to the mock treated controls at 1 hour post-training (FIG. 17B). However, 24 hours after training, mice were placed into the chamber for the second time to examine the effects of Reelin on long-term memory formation. Reelin-treated mice showed a significant increase in percent freezing compared to mock-treated controls (FIG. 17C). These levels are similar to the levels of freezing in WT mice that the inventors have previously shown (~70%), while the mock-treated controls resembled our HRM. This suggests that reelin rescues the hippocampal-dependent associative learning deficits seen in the HRM to resemble the WT mouse. When tested 72 hour following training, there is no statistical significance between the two treatment groups, although there is trend for an increase in freezing in the Reelin group compared to mock controls (FIG. 17D). This may represent a consolidation effect in some of the mice in that the re-introduction into the context in the absence of the aversive stimulus may lead to the recall and re-organization of the memory. The ensure that both treatment groups had similar sensitivities to the foot-shock, a shock threshold test was performed. No difference was seen between reelin-treated and mock-treated mice (FIG. 17E). Thus, Reelin replacement to the CNS of HRM rescues the contextual fear conditioning defect.

In Vivo Application of Receptor Associated Protein.

The results above show that increasing Reelin, and subsequent Reelin signaling, in the hippocampus rescues the cognitive deficit. If the decrease in ApoER2 and VLDLR signaling is responsible for the cognitive defects in HRM, then one should be able to mimic these behavioral changes by blocking ApoER2 and VLDLR. Receptor Associated Protein (RAP) serves as a molecular chaperone for the family of lipoprotein receptors allowing transport to the plasma membrane without premature binding to ligand. Applied exogenously, RAP binds to the extracellular portion of the lipoprotein receptor and acts as an effective antagonist. Exogenous application of RAP results in association of inserted receptors and can effectively block extracellular ligand-induced signaling. The use of RAP as a biological antagonist has previously been used to block receptor-induced signaling in culture and tissue, and can effectively block long-term potentiation (LTP) in wild-type hippocampus. Thus, the behavioral tests were performed on wild-type mice injected with 1 ul of concentrated GST-RAP or GST as a negative control.

Exogenous GST-RAP or GST (used as a negative control) ha no effect on overall behavior (FIGS. 18A and B-C) and no change was seen in PPI or acoustic startle (FIG. 18D-E). There were no changes in freezing during fear condition experiments or in testing to the context 1 hour after training (FIG. 19A-C). However, GST-RAP injection resulted in a significant decrease in freezing to the context to a level identical to that seen in our HRM Mock treated animals and those levels previously reported in HRM mice (FIG. 19C). No differences were seen in shock thresholds between the two treatment groups (FIG. 19D).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method of improving cognitive function in a subject comprising:
   administering a therapeutically effective amount of a Reelin fragment to a subject;
   wherein the Reelin fragment is a 450 kDa Reelin protein fragment, a 370 kDa Reelin protein fragment, a 180 kDa Reelin protein fragment, or a combination thereof to the subject.

2. The method of claim 1, wherein the subject suffers from a disease or disorder of the nervous system selected from the group consisting of fragile X syndrome, William's syndrome, Rett syndrome, Down's syndrome, Angelman syndrome, autism, ischemia, hypoxia, Alzheimer's disease, Reelin deficiency, schizophrenia and stroke.

3. The method of claim 2, wherein the disease or disorder of the nervous system is characterized by a symptom selected from the group consisting of a deficiency in dendritic spine density and diminished synaptic plasticity.

4. A method of improving cognitive function in a subject having a disease or disorder of a nervous system comprising:
   administering a therapeutically effective amount of a Reelin fragment to a subject;
   wherein the Reelin fragment is a 450 kDa Reelin protein fragment, a 370 kDa Reelin protein fragment, a 180 kDa Reelin protein fragment, a 190 kDa Reelin protein fragment, or a combination thereof to the subject; and
   wherein the disease or disorder of the nervous system is selected from the group consisting of fragile X syndrome, William's syndrome, Rett syndrome, Down's syndrome, Angelman syndrome, autism, ischemic, hypoxia, Alzheimer's disease, Reelin deficiency, schizophrenia, neurodegeneration, traumatic brain injury, mental retardation, dementia, and stroke.

5. The method of claim 4, wherein the disease or disorder of the nervous system is characterized by a symptom selected from the group consisting of a deficiency in dendritic spine density and diminished synaptic plasticity.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: artificial sequence
<220> FEATURE:
<223> OTHER INFORMATION: Forward Primer Sequence

<400> SEQUENCE: 1
taatctgtcc tcactctgcc                    20

<210> SEQ ID NO 2
<211> LENGTH: 20
<212> TYPE: DNA
<213> ORGANISM: artificial sequence
<220> FEATURE:

-continued

```
<223> OTHER INFORMATION: Reverse primer Sequence

<400> SEQUENCE: 2
acagttgaca taccttaatc                                              20

<210> SEQ ID NO 3
<211> LENGTH: 22
<212> TYPE: DNA
<213> ORGANISM: artificial sequence
<220> FEATURE:
<223> OTHER INFORMATION: Reverse mutated primer sequence

<400> SEQUENCE: 3
tgcattaatg tgcagtgttg tc                                           22
```